(12) United States Patent
Arteaga et al.

(10) Patent No.: US 10,701,509 B2
(45) Date of Patent: *Jun. 30, 2020

(54) EMULATING SPATIAL PERCEPTION USING VIRTUAL ECHOLOCATION

(71) Applicant: Microsoft Technology Licensing, LLC, Redmond, WA (US)

(72) Inventors: Brandon Myles Arteaga, Redmond, WA (US); Wilson Jacob Dreewes, Monroe, WA (US); Jeffrey Michael Davis, Redmond, WA (US); Zainuddin Qazi, Seattle, WA (US); Boris Eduardo Baracaldo Doikova, Seattle, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/415,414

(22) Filed: May 17, 2019

(65) Prior Publication Data

US 2019/0274001 A1  Sep. 5, 2019

Related U.S. Application Data

(63) Continuation of application No. 15/491,897, filed on Apr. 19, 2017, now Pat. No. 10,321,258.

(51) Int. Cl.
*H04S 7/00* (2006.01)
*H04R 5/033* (2006.01)
(Continued)

(52) U.S. Cl.
CPC .......... *H04S 7/304* (2013.01); *A61F 9/08* (2013.01); *G01S 15/42* (2013.01); *G01S 15/88* (2013.01);
(Continued)

(58) Field of Classification Search
None
See application file for complete search history.

(56) References Cited

U.S. PATENT DOCUMENTS 9,094,576 B1 *  7/2015  Karakotsios ........... H04N 7/157
9,406,170 B1 *  8/2016  Grampurohit ......... G06T 3/005
(Continued)

*Primary Examiner* — Ricky Chin
(74) *Attorney, Agent, or Firm* — Alleman Hall Creasman & Tuttle LLP

(57) ABSTRACT

Examples are disclosed that relate to a head-mounted device configured to perform virtual echolocation. The head-mounted device is configured to cast an array of rays at specified angles from a position derived from a pose of the head-mounted device in a physical environment, identify a plurality of intersection points of the rays with a virtual model of the physical environment, for each identified intersection point, modify an audio signal based on a head-related transfer function corresponding to the intersection point to produce a plurality of spatialized audio signals, for each spatialized audio signal, determine a time-of-flight adjustment based upon a distance between the corresponding intersection point and the position from which the rays were cast, and output each spatialized audio signal to one or more speakers with a delay based on the time-of-flight adjustment.

20 Claims, 11 Drawing Sheets

(51) Int. Cl.
*G06T 19/00* (2011.01)
*G06F 3/01* (2006.01)
*H04N 13/204* (2018.01)
*A61F 9/08* (2006.01)
*G01S 15/42* (2006.01)
*G01S 15/88* (2006.01)
*G09B 21/00* (2006.01)

(52) U.S. Cl.
CPC ............ *G06F 3/012* (2013.01); *G06T 19/006* (2013.01); *G09B 21/006* (2013.01); *H04N 13/204* (2018.05); *H04R 5/0335* (2013.01); *H04S 2400/01* (2013.01); *H04S 2400/11* (2013.01); *H04S 2420/01* (2013.01)

(56) References Cited

U.S. PATENT DOCUMENTS

| | | | |
|---|---|---|---|
| 10,321,258 B2* | 6/2019 | Arteaga | H04S 7/304 |
| 2016/0070356 A1* | 3/2016 | Aguirre | H04N 13/337 345/156 |
| 2016/0209916 A1* | 7/2016 | Sendai | G02B 27/0093 |
| 2016/0261300 A1* | 9/2016 | Fei | H04W 4/70 |
| 2016/0266865 A1* | 9/2016 | Tsingos | H04S 7/304 |
| 2016/0336022 A1* | 11/2016 | Florencio | G10K 11/002 |
| 2017/0005465 A1* | 1/2017 | Wyland | G01S 7/484 |
| 2017/0332186 A1* | 11/2017 | Riggs | G06F 3/012 |
| 2018/0204160 A1* | 7/2018 | Chehade | H04L 67/36 |
| 2018/0295461 A1* | 10/2018 | Di Censo | H04S 3/008 |
| 2018/0310116 A1* | 10/2018 | Arteaga | H04S 7/304 |

* cited by examiner

US 10,701,509 B2

EMULATING SPATIAL PERCEPTION USING VIRTUAL ECHOLOCATION

CROSS REFERENCE TO RELATED APPLICATIONS

This application is a continuation of U.S. patent application Ser. No. 15/491,897, filed Apr. 19, 2017, the entire contents of which is hereby incorporated herein by reference for all purposes.

BACKGROUND

Echolocation is the process by which an individual can perceive his or her surroundings by emitting an acoustic pulse and listening for the reflection of the sound waves from nearby surfaces. Many animals, such as bats, use this technique effectively to navigate complex environments at high speed in low-light conditions. Echolocation also may be utilized by some members of the visually impaired community to navigate various environments.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

Examples are disclosed that relate to a head-mounted device configured to perform virtual echolocation. The head-mounted device is configured to cast an array of rays at specified angles from a position derived from a pose of the head-mounted device in a physical environment, identify a plurality of intersection points of the rays with a virtual model of the physical environment, for each identified intersection point, modify an audio signal based on a head-related transfer function corresponding to the intersection point to produce a plurality of spatialized audio signals, for each spatialized audio signal, determine a time-of-flight adjustment based upon a distance between the corresponding intersection point and the position from which the rays were cast, and output each spatialized audio signal to one or more speakers with a delay based on the time-of-flight adjustment.

DETAILED DESCRIPTION

Figure 1:
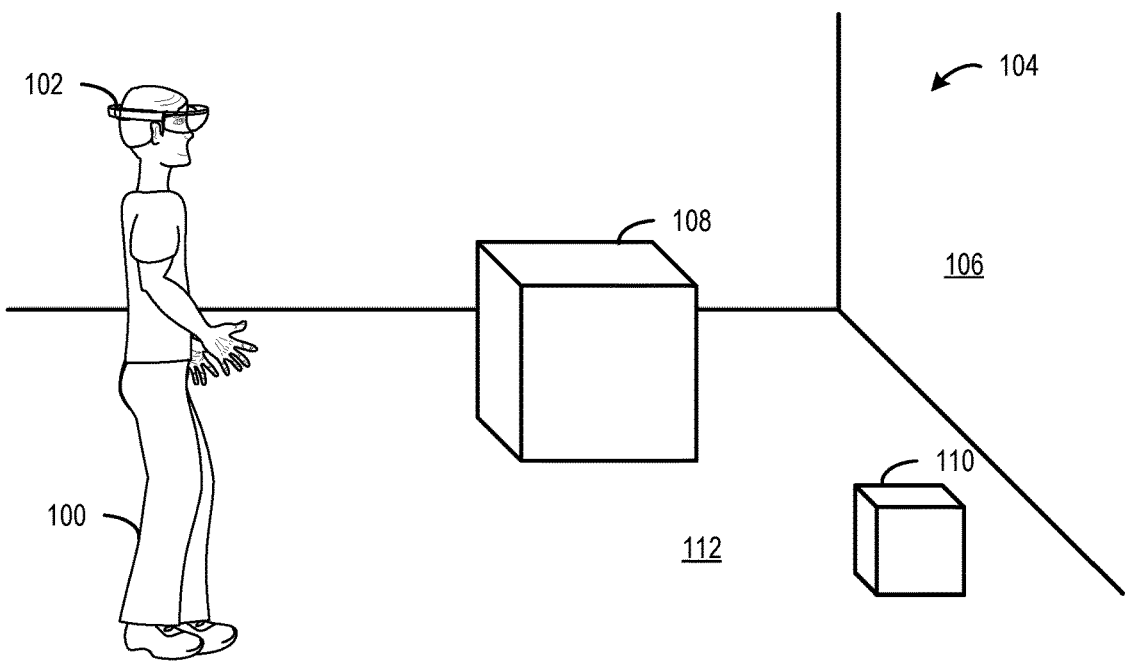
FIG. 1 shows a wearer of an example head-mounted device interacting with a physical environment.

Near-field navigation and contextual understanding of one's place in a larger setting are both challenges that members of the visually impaired community face on a daily basis. Without the benefit of sight, navigating safely in unfamiliar environments can be quite difficult and certain obstacles may be hard to detect. This problem becomes compounded when the rate of movement is increased. In one example, a navigation aid device uses a laser distance meter to provide one-dimensional feedback on the distance of an object to the device. The device outputs audio feedback in the form of "beeps" or haptic feedback in the form of vibrations. The device works in a similar manner to a traditional cane that is held by a user, but the device replaces the physical rod of the traditional cane with a single laser beam. In this way, the device can detect objects that are located farther away than a traditional cane. However, the device is required to be pointed directly at an object in order for the laser beam to detect the object. Such a one-dimensional scanning approach may be too slow and may not provide detailed enough spatial feedback to successfully navigate a real-world physical environment.

Accordingly, examples are disclosed that relate to a head-mounted device configured to perform virtual echolocation using a multi-dimensional scanning approach. More particularly, the head-mounted device may be configured to generate a virtual model of a physical environment based on depth images provided from a depth camera of the head-mounted device, cast an array of rays from a point derived from a position of the head-mounted device in the physical environment, and locate spatialized audio sources at intersection points of the rays with the virtual model. The spatialized audio sources may emulate virtual audio speakers located at the different intersection points in the physical environment. The head-mounted device may be further configured to output time-of-flight adjusted, spatialized audio signals corresponding to the different spatialized audio sources to one or more speakers of the head-mounted device. The time-of-flight adjustment of each of the spatialized audio signals may be based upon a distance between the location of the intersection point/virtual audio speaker and the position from which the ray was cast. The spatialized audio signals may communicate detailed geometric information about the physical environment that may be used by the wearer of the head-mounted device to create a three-dimensional (3D) map of the surrounding physical environment in his or her visual cortex. The head-mounted device may be configured to repeatedly output the spatialized audio signals that allow the wearer to form an updated 3D map in his or her visual cortex such that the wearer can freely investigate the surrounding physical environment in real-time.

By casting out an array including a plurality of rays at different angles into the physical environment, multiple spatialized audio signals may be output, which may enable the wearer of the head-mounted device to form a detailed 3D map of the physical space in his or her visual cortex. Furthermore, by performing the time-of-flight adjustment, the spatialized audio signals may be output with corresponding delays that accurately reflect the position of the virtual audio sources in the physical environment. Moreover, because the time-of-flight adjustment is based upon a simple distance calculation, the time-of-flight adjustment can be performed fast enough for the head-mounted device to output the time-of-flight adjusted, spatialized audio signals according to designated refresh rate or cadence (e.g., in real time). In other words, such a head-mounted device may deliver complex spatial audio information to a wearer of the head-mounted device in a way that is easily assimilated and can be rapidly consumed.

FIG. 1 shows a user (or wearer) 100 wearing a head-mounted device 102 in a physical environment 104. The head-mounted device 102 is configured to facilitate virtual echolocation by outputting a plurality of audio signals that correspond to a plurality of virtualized audio sources located at different positions/surfaces in the physical environment 104. For example, the wearer 100 may be visually impaired (e.g., blind), and the virtual echolocation provided by the head-mounted device 102 may help the wearer 100 avoid objects in the physical environment 104 and otherwise navigate the physical environment 104. In other examples, the head-mounted device 102 may be worn by a user that is not visually impaired for navigation purposes. For example, the virtual echolocation provided by the head-mounted device 102 may help the user navigate a physical environment in low-light conditions or in the dark. In still another example, the head-mounted device 102 may be used to aid the wearer 100 in navigating a virtual environment (e.g., in a video game) via virtual echolocation that maps the physical features of the virtual environment to time-of-flight adjusted, spatialized audio signals that characterize the virtual environment.

In the illustrated example, the head-mounted device 102 may provide virtual echolocation that enables the wearer 100 to recognize a position of the wearer 100 relative to different physical features in a room. For example, the wearer 100 may recognize how far away he is standing from a wall 106. Furthermore, the wearer 100 may recognize the positions of a large block 108 and a small block 110 on a floor 112 relative to the position of the wearer 100 in the physical environment 104.

Figure 2:
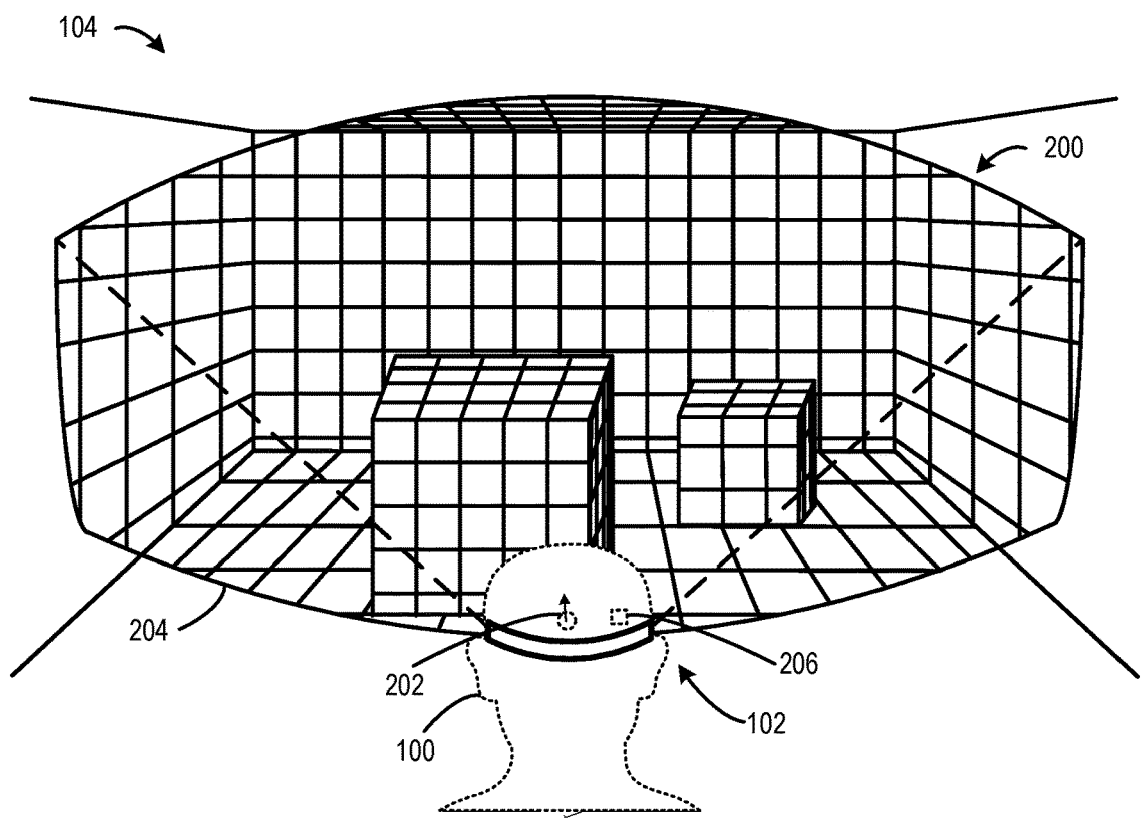
FIG. 2 shows the head-mounted device of FIG. 1 generating an example virtual model of the physical environment.

To provide virtual echolocation for the wearer 100, the head-mounted device 102 is configured to generate a virtual model of the physical environment 104 in which spatialized audio sources can be placed. FIG. 2 schematically shows an example virtual model 200 of the physical environment 104 from a perspective of the wearer 100. The virtual model 200 may be generated by the head-mounted device 102 in any suitable manner. In one example, the head-mounted device 102 includes one or more high-resolution depth sensing cameras 202 configured to image the physical environment 104. The head-mounted device 102 may be configured to generate the virtual model 200 based on one or more depth images from the depth sensing camera(s) 202. In the illustrated example, the virtual model 200 takes the form of a wire-frame mesh representing all objects and surfaces in the physical environment 104. In one example, the wire-frame mesh may include up to 1200 triangles per cubic meter that provides high-density, accurate modeling of the physical environment 104. Because the virtual model 200 is generated based on the depth image(s) from the depth sensing camera 202, the wire-frame mesh 200 may cover at least an entire field of view 204 of the depth sensing camera 202.

In some implementations, the virtual model 200 may be of a virtual environment (e.g., a video game). In such implementations, the head-mounted device 200 may provide virtual echolocation to aid in navigation of the virtual environment. For example, the head-mounted device 102 may be used by a seeing-impaired wearer to play a video game.

Furthermore, the head-mounted device 102 may include one or more motion sensors 206, such as an inertial measurement unit (IMU), configured to measure one or more motion parameters. The head-mounted device 102 may be configured to determine a pose (e.g., three-dimensional (3D) position) of the head-mounted device 102 in the physical environment 104 in relation to the virtual model 200 based on the motion parameter(s) of the motion sensor(s). In one example, the head-mounted device 102 is configured to perform simultaneous localization and mapping (SLAM) based on sensor feedback from the depth sensing camera(s) 202 and the motion sensor(s) 206. The head-mounted device 102 may employ SLAM to rapidly update (e.g., in real time) the virtual model 200 and the pose of the head-mounted device 102 to accurately reflect movement of the head-mounted device 102/wearer 100 as well as other objects in the physical environment 104.

In some implementations, the head-mounted device 102 may be configured to store the virtual model 200 in a "world map" repository once the virtual model 200 is generated. The world map repository may be stored locally or remotely (e.g., sent to a remote cloud storage system). The world map repository may aggregate various virtual models of different real-world locations generated by the head-mounted device 102 and/or other head-mounted devices worn by other wearers that move about the physical environment 104. For example, the head-mounted device 102 may be configured to reference/retrieve the virtual model 200 when the head-mounted device 102 has traveled away from the position in the physical environment 104 a distance that is outside of an active refresh radius of the depth camera(s) for model/position information.

To provide virtual echolocation for the wearer 100, the head-mounted device 102 is configured to cast an array of virtual vector rays into the physical environment 104. FIGS.

Figure 3:
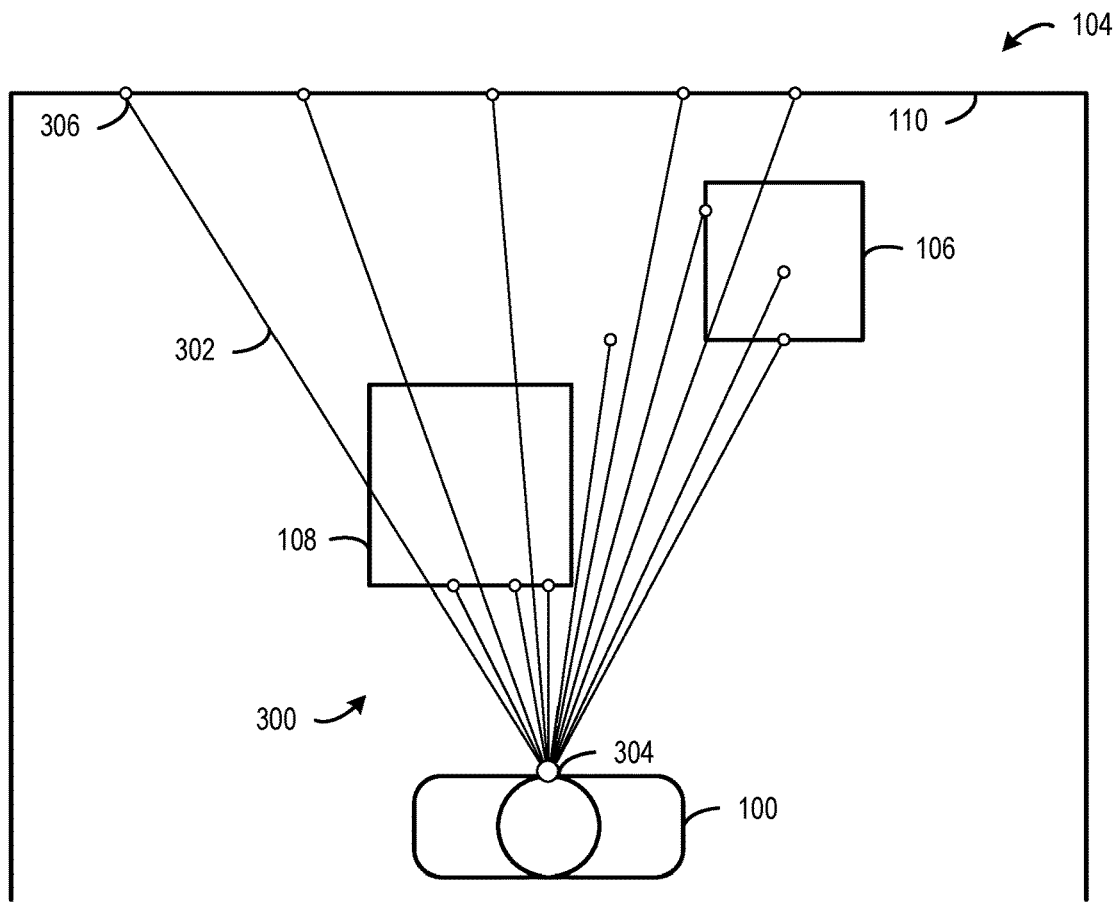
FIGS. 3 and 4 schematically show the head-mounted device of FIG. 1 casting an array of rays into the physical environment.
Figure 4:
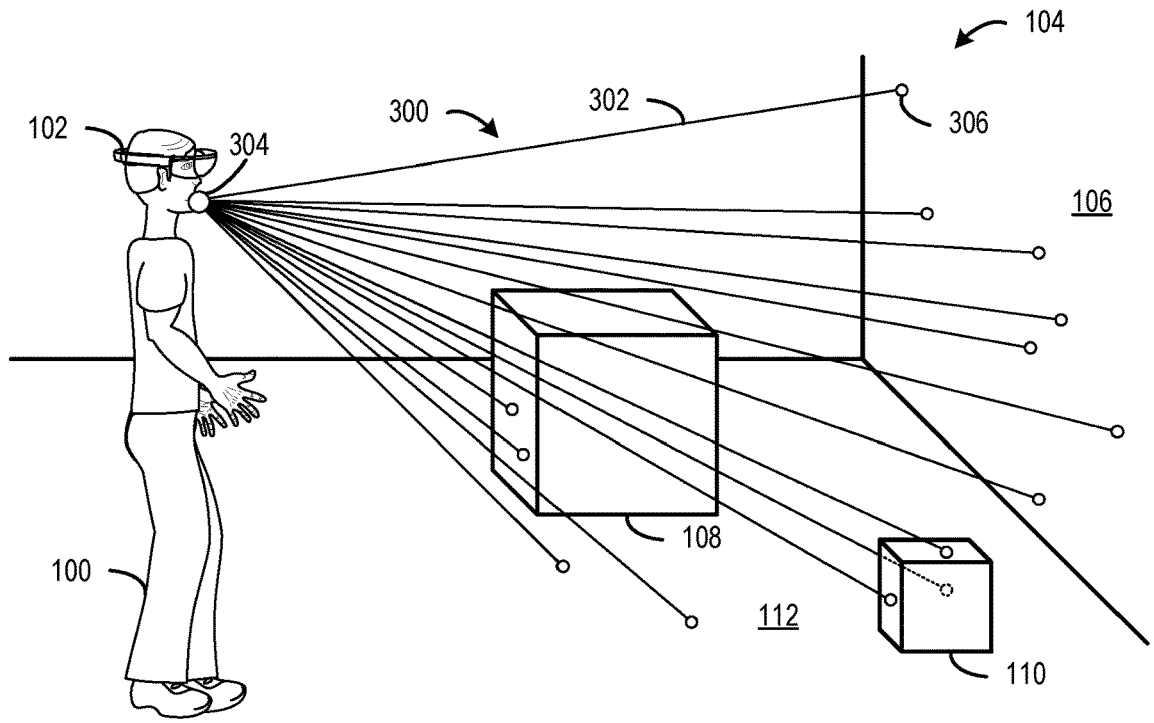

3 and 4 schematically show an example array 300 of rays 302 cast out by the head-mounted device 102 into the physical environment 104. FIG. 3 shows an overhead view of the physical environment 104. FIG. 4 shows a side view of the physical environment 104. The head-mounted device 102 is configured to cast out the array 300 of rays 302 at specified angles from an origin position 304 derived from the determined pose of the head-mounted device 102. The head-mounted device 102 may be configured to cast out the array 300 of rays 302 from any suitable origin position. In this example, the origin position approximates the wearer's mouth. For example, the origin position may be determined based upon a designated offset from the determined pose of the head-mounted device 102. In one example, the offset is calculated based on an average distance between the position of the head-mounted device and a wearer's mouth for a population of users.

The array 300 may include any suitable number of rays 302. In one example, the array 300 includes thirty rays cast out from the origin position 304. The different rays 302 may be cast out at any suitable angle from the origin position 304 into the physical environment 104. For example, each ray 302 may be cast with a fixed angular offset that is shifted from a reference vector to form a consistent pattern (e.g., a cone). In another example, each ray 302 may be cast with a different angular offset to form a randomized pattern. In yet other examples, rays may be selected to have a closer angular proximity in regions of a virtual model with a greater density of features (e.g. furniture, angles or discontinuities in walls, etc.), and a wider angular separation in regions of the virtual model with a lower density of features.

Each of the rays 302 in the array 300 may extend from the origin position 304 to an intersection point 306 of a surface in the physical environment 104. The head-mounted device 102 may be configured to identify the plurality of intersection points 306 using the virtual model 200. When the virtual model 200 is active, the head-mounted device 102 may be configured to recognize the intersection points 306 at which the rays 302 collide with the virtual model 200. For example, the origin position 304 and the intersection points 306 may be represented by 3D coordinates having a frame of reference that is relative to the virtual model 200.

The head-mounted device 102 may be configured to generate spatialized audio signals that originate from virtual audio sources positioned at each of the intersection points 306. For example, the head-mounted device 102 may be configured to, for each intersection point of the plurality of intersection points 306, modify an input audio signal based on a head related transfer function (HRTF) corresponding to the intersection point 306 to produce the spatialized audio signal corresponding to the intersection point 306. The HRTF modifies the input audio signal to account for the changes in volume and directionality of the audio signal based on the simulated position from which the audio signal originates in the physical environment 104.

Furthermore, the different intersection points 306 may be different distances from the origin position 306 based on where the corresponding rays 302 intersect the surfaces of different objects in the physical environment 104. In the illustrated example, some longer rays extend from the origin position 304 to intersection points on the wall 106. Other shorter rays extend from the origin position 304 to intersection points on the large block 108, the small block 110, as well as on the floor 112. The head-mounted device 102 may be configured to, for each ray 302 in the array 300, determine a distance from the origin position 304 to the corresponding intersection point 306 of the ray 302. The head-mounted device 102 may be configured to, for each spatialized audio signal of the plurality of spatialized audio signals corresponding to the plurality of intersection points 306, determine a time-of-flight adjustment based upon the distance. The time-of-flight adjustment accounts for the time it takes the audio signal to travel from the user's mouth to the intersection point, and then back to the user's ears based upon the speed of sound. In the illustrated example, the time-of-flight adjustment may be larger for intersection points located on the wall 106 relative to intersection points located on the large box 108. Since the time-of-flight adjustment is based upon a simple distance calculation, the time-of-flight adjustment may be performed quickly while using minimal processing resources. In this way, the head-mounted device 102 may provide spatialized audio signals that accurately characterize the physical environment 104 in substantially real-time.

In some cases, a spatialized audio signal may be output from the speakers according to a delay that is exaggerated relative to the time-of-flight adjustment to aid the user in recognizing the audio signal. For example, the delays associated with the spatialized audio signals may be increased during a training mode in order to make it easier for a user to learn the technique. Once the user becomes proficient with echolocation, the delays may be adjusted to correspond to the time-of-flight adjustments.

Figure 5:
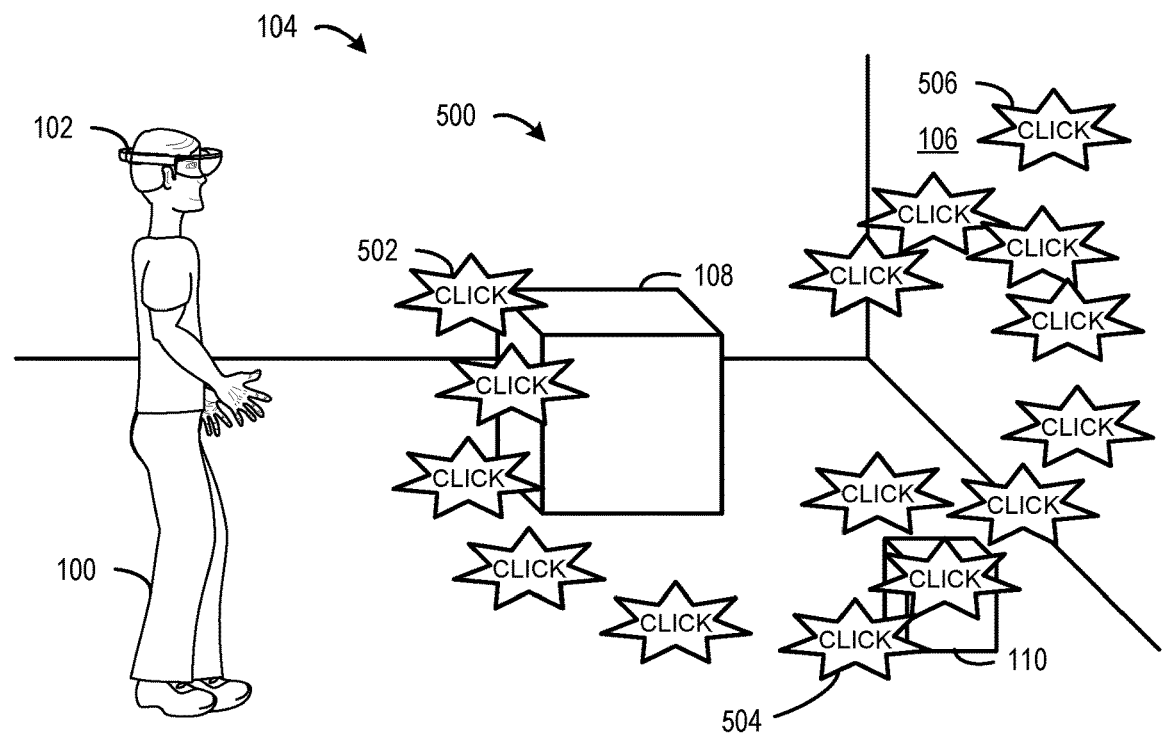
FIG. 5 shows the head-mounted device of FIG. 1 outputting time-of-flight adjusted, spatialized audio signals corresponding to different intersection points of the virtual model of the physical environment.

The head-mounted device 102 may be configured to output the spatialized audio signals to one or more of a left ear speaker and a right ear speaker of the head-mounted device 102 with a delay corresponding to the time-of-flight adjustment. For example, in FIG. 5, the speakers of the head-mounted device 102 output a plurality of spatialized audio signals 500 in the form of impulsive "clicking" sounds. For simplicity, the impulsive clicking sounds are depicted as occurring at the same time. In actuality, the impulsive clicking sounds are output over a window of time. In particular, each impulsive clicking sound is output with a different volume and delay based on the HRTF and the time-of-flight adjustment to give the wearer 100 the impression that the clicking sound originated from the corresponding intersection point in the physical environment 104. The HRTF accounts for the difference in sound communicated to each ear from each sound source based on the individual wearer's ears relative to the position to the audio source. For example, an audio signal received from a virtual audio source positioned on a right side of the wearer is output with a higher volume in the right ear speaker than in the left ear speaker because the wearer's head partially occludes the virtual audio source from the left ear.

For example, in the illustrated scenario, a first clicking sound 502 originating from the large box 108 may be output with a high volume and short delay to indicate that the large box is proximate to the wearer 100. A second clicking sound 504 originating from the small box 110 may be output with a lower volume and a longer delay than the first click 502 to indicate that the small box 110 is further away from the wearer 100 than the large box 108. A third clicking sound 506 originating from the wall 106 may be output with a still lower volume and a still longer delay than the second click 504 to indicate that the wall 106 is further away from the wearer 100 than the small box 106. Each clicking sound may be experienced uniquely by the wearer 100 to communicate the position of all virtual audio sources in the physical environment 104. Moreover, each clicking sound may have a unique volume and delay associated with the 3D position in the physical environment of the corresponding virtual audio source from which the clicking sound originated.

The audio signal that produces the clicking sound may be designed for high neuro-native reception to make it feel natural to the wearer. Such high neuro-native reception allows the audio information to be easily digested by the wearer subconsciously, so that the wearer can quickly interpret the spatialized audio signals to assemble a three-dimensional model in the wearer's visual cortex. In one example, the clicking sound is characterized as an impulse response of a transfer function between the human mouth and ear, as captured on a Head and Torso Simulator (HATS). This stimulus is short, with high power, fast decay, and frequency content focused in the 2-3 kHz region, where human hearing is sensitive and spatial cues are easy to discriminate. The clicking sound is provided as an example of an audio signal that is meant to be non-limiting. The head-mounted device 102 may be configured to output any suitable type of audio signal to provide virtual echolocation to a user.

Figure 6:
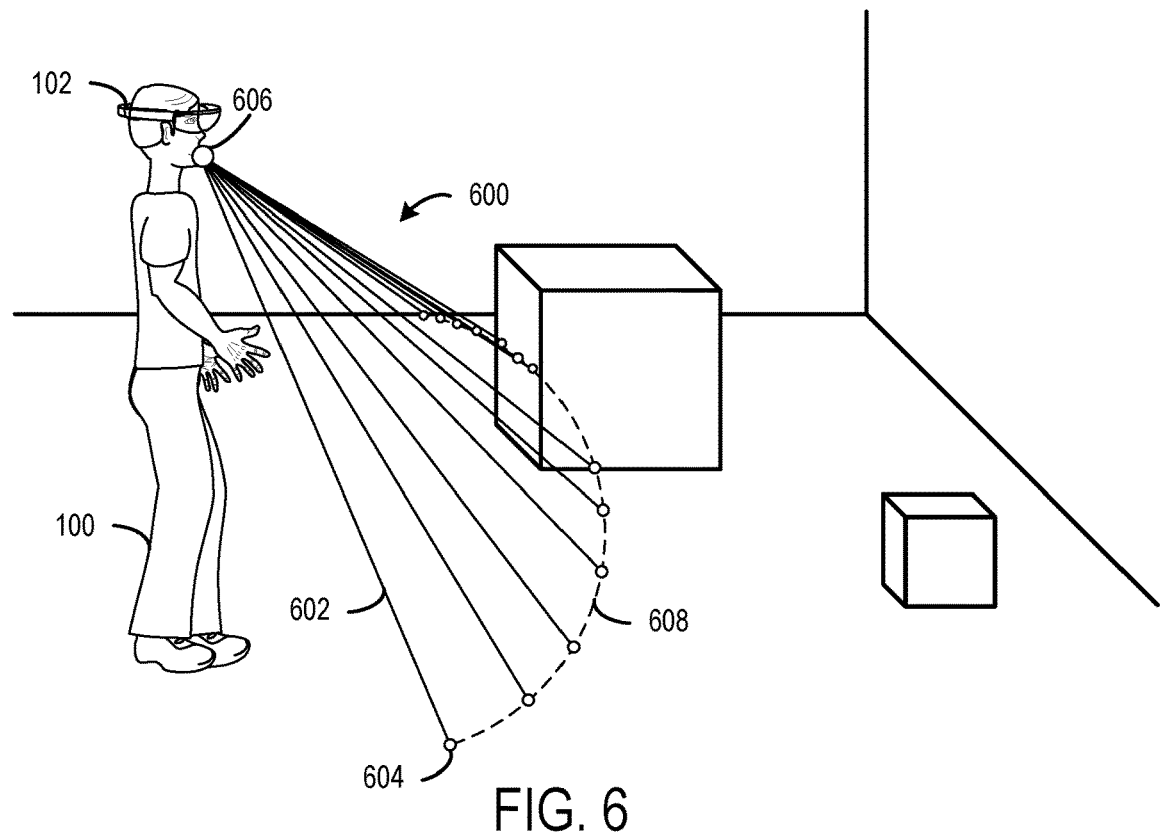
FIG. 6 shows an example head-mounted device casting an array of rays at specified angles into a physical environment to form a virtual echolocation cane.

In some implementations, the head-mounted device 102 may be configured to cast an array of rays each having a fixed length and at specified angles to form a virtual echolocation "cane" to aid navigation of the wearer 100. FIG. 6 shows an example array 600 including a plurality of rays 602 each having the same length and cast at different angles. The array 600 of rays 602 are cast downward at a thirty-degree angle from the origin position 606 that approximates the user's mouth to form a semicircular perimeter 608 in front of the user 100. Note that the rays 602 in the array 600 may have any suitable length and may be cast at any suitable angle from the origin position 606. The head-mounted device 102 may be configured to output time-of-flight adjusted, spatialized audio signals corresponding to intersection points of each of the rays 602 in the array 600 with the virtual model. Since each of the rays 602 are the same length, the array 600 of rays 602 can detect objects that are positioned a designated distance (e.g., several feet) in front of the user 100. For example, this a mode of operation may be used to identify any tripping hazards, center the wearer in a hallway, and/or aid in navigation in other manners. In some cases, if no object intersects a particular ray, then the head-mounted device 102 does not output a spatialized audio signal corresponding to the ray. In other words, the head-mounted device 102 only provides audio feedback if an object enters the perimeter 608 of the virtual cane in this example.

This virtual cane mode of operation may be used alternatively or in addition to the virtual echolocation mode in which the rays do not have a fixed length. In some implementations, the virtual cane may have a different audio signal than the virtual echolocation such that the wearer 100 may be able to differentiate between the two forms of audio feedback. For example, the head-mounted device 102 may output clicking sounds for the virtual echolocation and output "buzzer" sounds if a tripping hazard enters the perimeter 608 formed by the virtual cane. Any suitable different audio signals may be used to provide audio feedback for virtual echolocation and virtual cane modes of operation.

Figure 7:
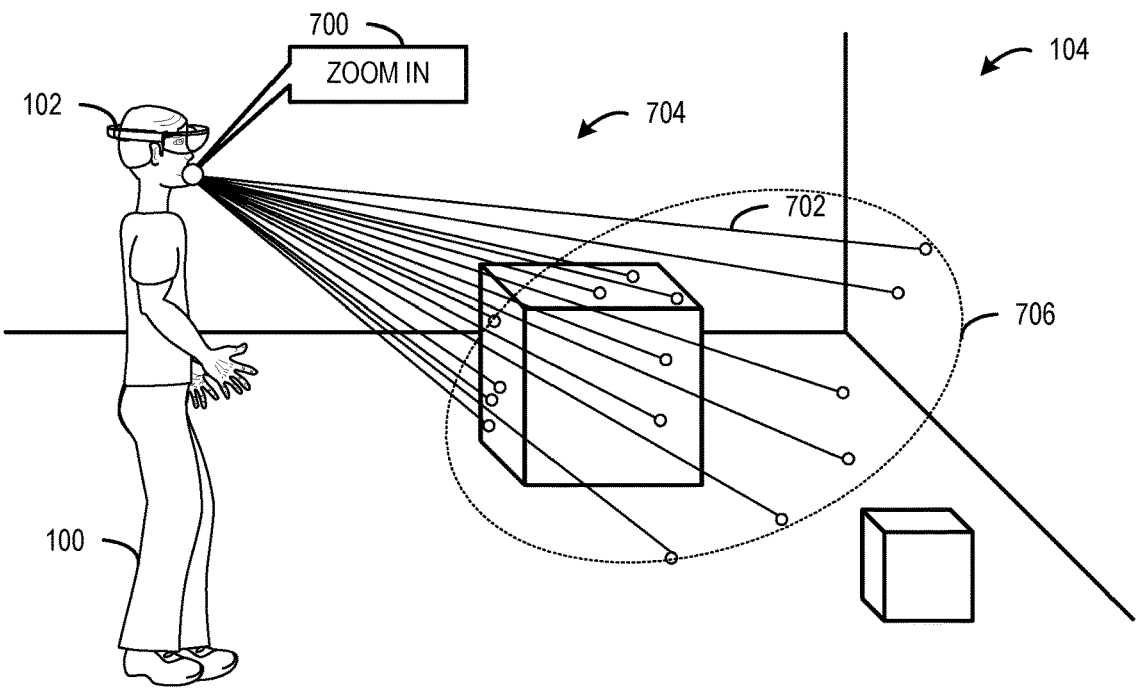
FIG. 7 shows an example head-mounted device casting an array of rays at specified angles that cover a smaller region of coverage of a physical environment based upon a voice command provided by a wearer of the head-mounted device.
Figure 8:
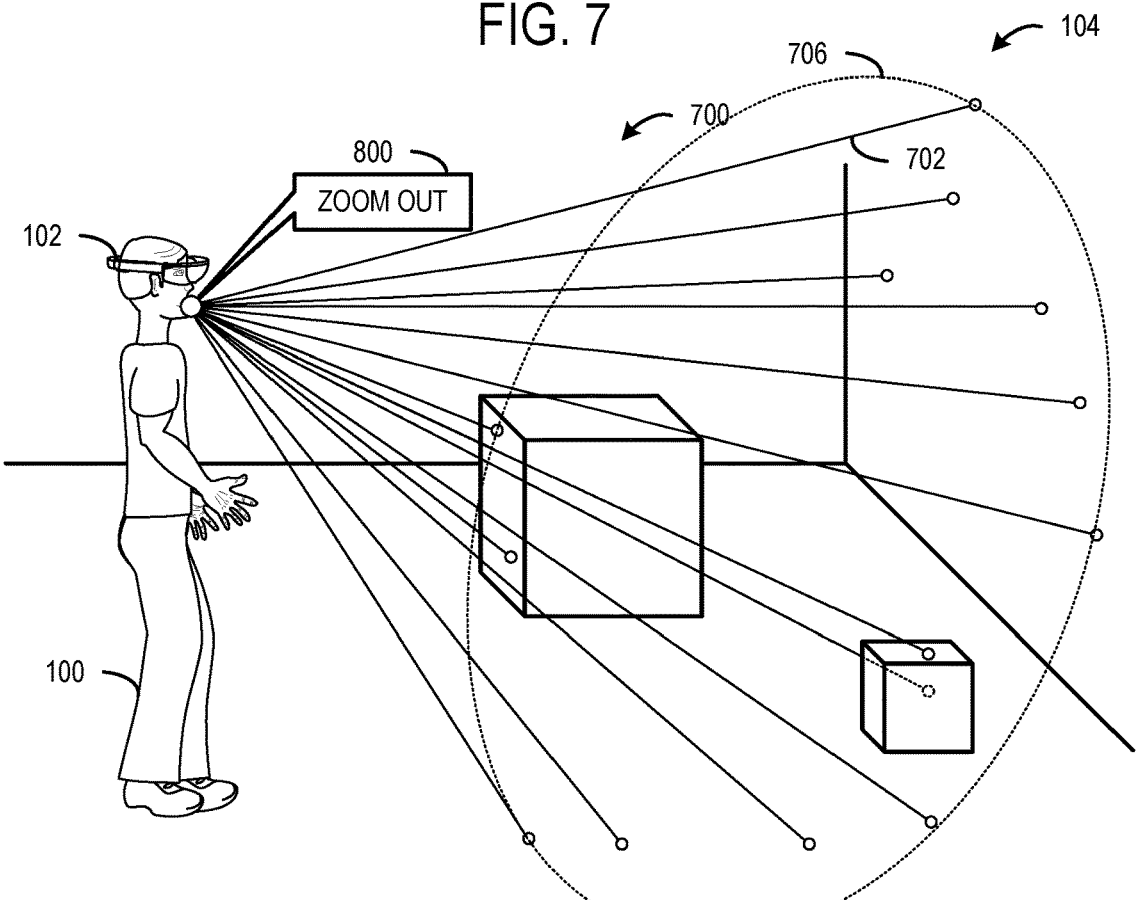
FIG. 8 shows an example head-mounted device casting an array of rays at specified angles that cover a larger region of coverage of a physical environment based upon a voice command provided by a wearer of the head-mounted device.

In some implementations, the head-mounted device may be configured to dynamically adjust the coverage region of the physical environment covered by the array of rays. FIGS. 7-10 show example scenarios in which the head-mounted device dynamically adjusts the coverage region of the array of rays. First, FIGS. 7-8 show example scenarios in which the head-mounted device 102 is configured to dynamically adjust the region of coverage of the array of rays based upon user input received from the wearer 100. In FIG. 7, the head-mounted device 102 detects a voice command 700 from the wearer 100 in the form of the phrase "zoom in." The head-mounted device 102 is configured to dynamically adjust the specified angles of the rays 702 in the array 704 based upon receiving the voice command from the wearer 100. In this example, the head-mounted device 102 adjusts the angles of the rays 702 to shrink a coverage region 706 of the physical environment 104 coved by the array 704. By shrinking the coverage region 706, the virtual audio sources may be concentrated to provide more detailed audio feedback in the coverage region. For example, the wearer 100 may shrink the coverage region 706 in real time when searching for an object in the coverage region 706.

In FIG. 8, the head-mounted device 102 detects a voice command 800 from the wearer 100 in the form of the phrase "zoom out." The head-mounted device 102 is configured to dynamically adjust the specified angles of the rays 702 in the array 704 based upon receiving the voice command from the wearer 100. In this example, the head-mounted device 102 adjusts the angles of the rays 702 to increase the coverage region 706 of the physical environment 104 coved by the array 704. By increasing the coverage region 706, the virtual audio sources may be dispersed to provide audio feedback characterizing more of the physical environment 104, albeit with less detail. For example, the wearer 100 may increase the coverage region 706 on the fly when moving throughout the physical environment 104.

The head-mounted device 102 may be configured to dynamically adjust the coverage region 706 of the array 704 based on receiving any suitable type of user input. In another example, the head-mounted device 102 may dynamically adjust the coverage region of the array based on detecting a gesture performed by the wearer. In yet another example, the head-mounted device 102 may dynamically adjust the coverage region of the array based on receiving user input from a user-input device, such as a clicker device.

Figure 9:
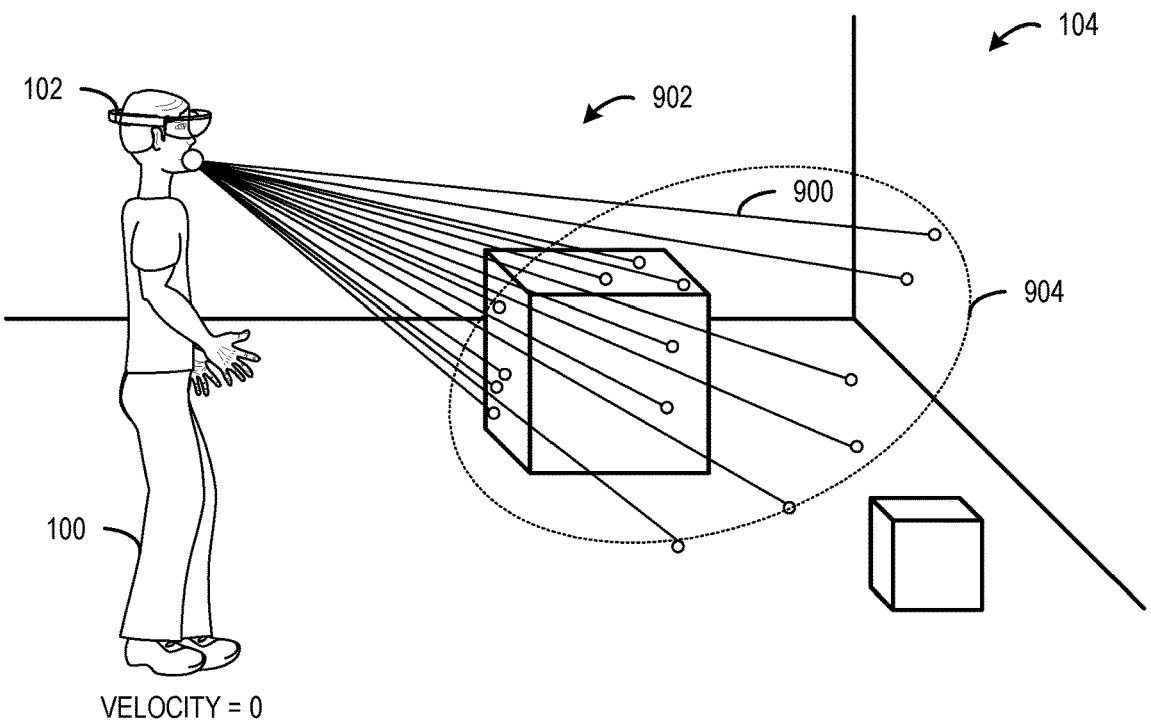
FIG. 9 shows an example head-mounted device casting an array of rays at specified angles that cover a small region of coverage of a physical environment based upon one or more motion parameters of one or more motion sensors of the head-mounted device.
Figure 10:
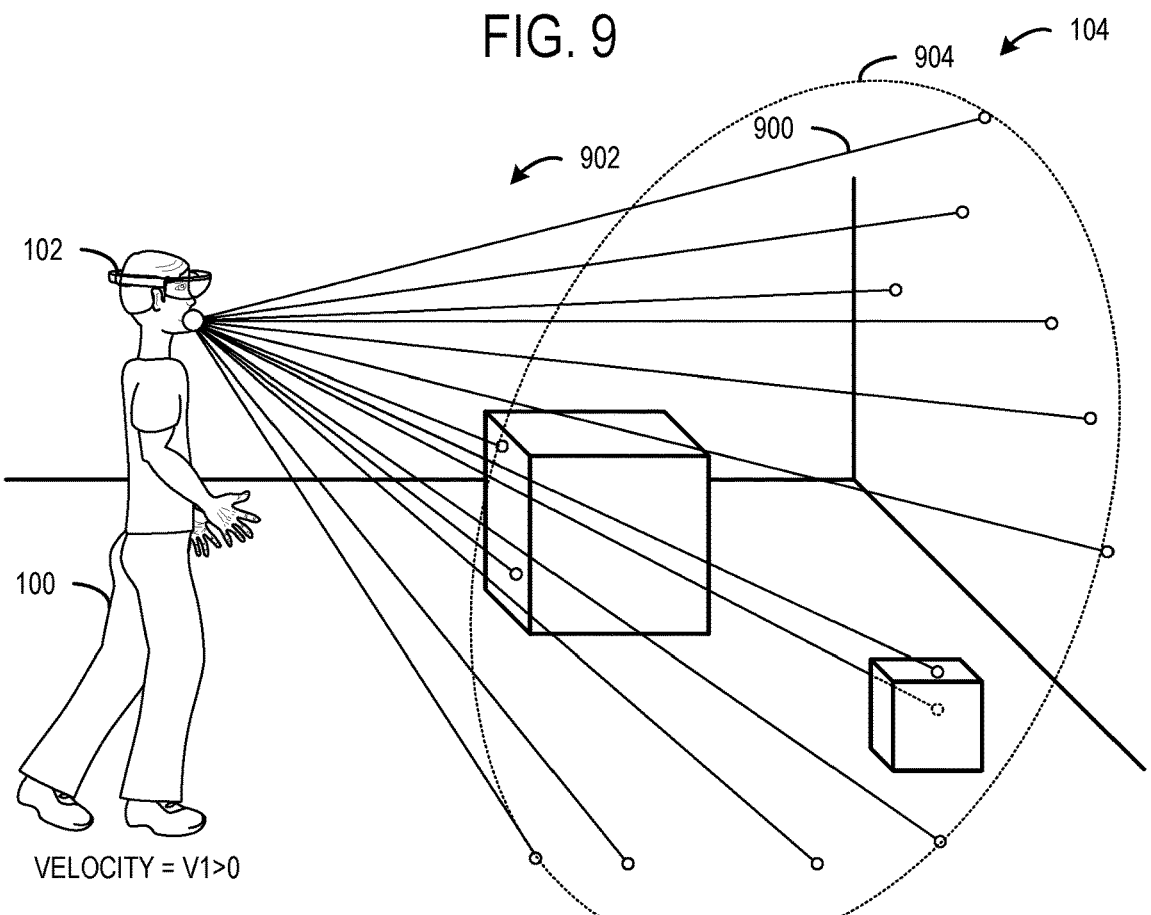
FIG. 10 shows an example head-mounted device casting an array of rays at specified angles that cover a large region of coverage of a physical environment based upon one or more motion parameters of one or more motion sensors of the head-mounted device.

FIGS. 9-10 show example scenarios in which the head-mounted device 102 is configured to dynamically adjust the region of coverage of the array of rays based upon one or more motion parameters of one or more motion sensors of the head-mounted device. In FIG. 9, a motion sensor of the head-mounted device 102 indicates that the velocity of the head-mounted device 102 is zero. In other words, the wearer 100 is standing still. The head-mounted device 102 is configured to dynamically adjust the specified angles of the rays 900 in the array 902 based upon the velocity. In this example, because the velocity is zero, the head-mounted device 102 adjusts the angles of the rays 900 to shrink a coverage region 904 of the physical environment 104 covered by the array 902.

In FIG. 10, the motion sensor of the head-mounted device 102 indicates that the velocity of the head-mounted device 102 is V1 which is greater than zero. In other words, the wearer 100 is moving throughout the physical environment 104. The head-mounted device 102 is configured to dynamically adjust the specified angles of the rays 900 in the array 902 based upon the velocity. In this example, because the velocity is greater than zero, the head-mounted device 102 adjusts the angles of the rays 900 to increase the coverage region 904 of the physical environment 104 covered by the array 902.

The head-mounted device 102 may be configured to adjust the coverage region of the array of rays based on any suitable motion parameter(s). Non-limiting examples of such motion parameters include velocity, acceleration, and angular acceleration. Further, the head-mounted device 102 may be configured to adjust the coverage region of the array of rays based on any suitable change of the motion parameter(s). In one example, the coverage region may be dynamically increased based on the velocity becoming greater than a threshold velocity. In another example, the coverage region may be dynamically changed linearly or non-linearly as the velocity changes.

The head-mounted device 102 may change the specified angles of the rays in the array to form any suitable shape of coverage region. In some implementations, the shape of the coverage region may be matched to the shape of the physical environment. For example, if the wearer is walking down a hallway, then the coverage region may be rectangular to match the dimensions of the hallway. In another example, the shape of the coverage region may surround the wearer. For example, the rays in the array may be cast out three hundred sixty degrees rotationally such that the rays are cast in all directions from the origin point. Such a coverage region may provide a low-detail characterization of the surrounding environment. In one example, such a coverage region may be employed to initially characterize a new space, such as when the wearer enters a room.

In some implementations, the head-mounted device 102 may be configured to change the number of rays included in the array when increasing/decreasing the coverage region of the array. For example, the head-mounted device 102 may increase the number of rays in the array when decreasing the coverage region to provide highly detailed audio feedback of the coverage region.

Additionally, in some implementations, the head-mounted device 102 may be configured to dynamically adjust the specified angles of the rays in the array based upon a position of a detected object in the physical environment nearest to the pose of the head-mounted device. For example, the nearest detected object may be assumed to be an object of interest to the wearer and the coverage region may be adjusted to focus on the object of interest.

Further, in some implementations, the head-mounted device 102 may be configured to dynamically adjust the specified angles of the rays in the array based upon a pose vector of the head-mounted device. For example, if the pose vector is directed towards a position close to the wearer, such as an area on the ground near the wearer, then the coverage region may be decreased to focus on that particular area on the ground. In another example, if the pose vector is directed towards a position away from the wearer, such as in the sky or along the horizon, then the coverage region may be increased.

In some implementations, the head-mounted device may be configured to dynamically adjust the refresh rate at which the time-of-flight adjusted, spatialized audio signals are repeatedly output to the speakers. Further, the virtual model may be continually updated and built upon as new rays are cast into the physical environment to determine appropriate intersection points corresponding to the position of the wearer in relation to the virtual model at each instant in time.

Figure 11:
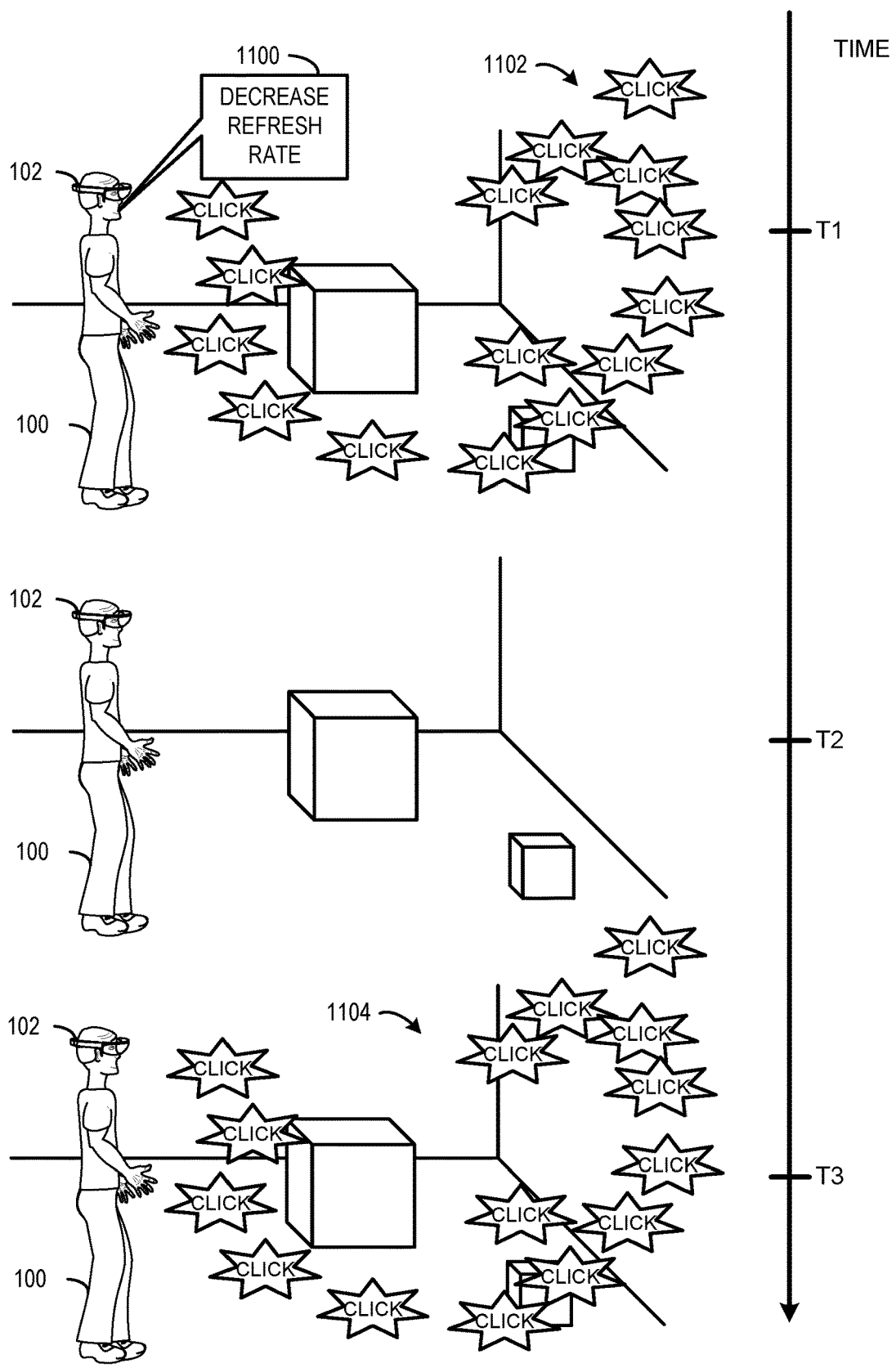
FIGS. 11 and 12 shows an example head-mounted device repeatedly outputting time-of-flight adjusted, spatialized audio signals according to a refresh rate that dynamically changes based upon a voice command provided by a wearer of the head-mounted device.
Figure 12:
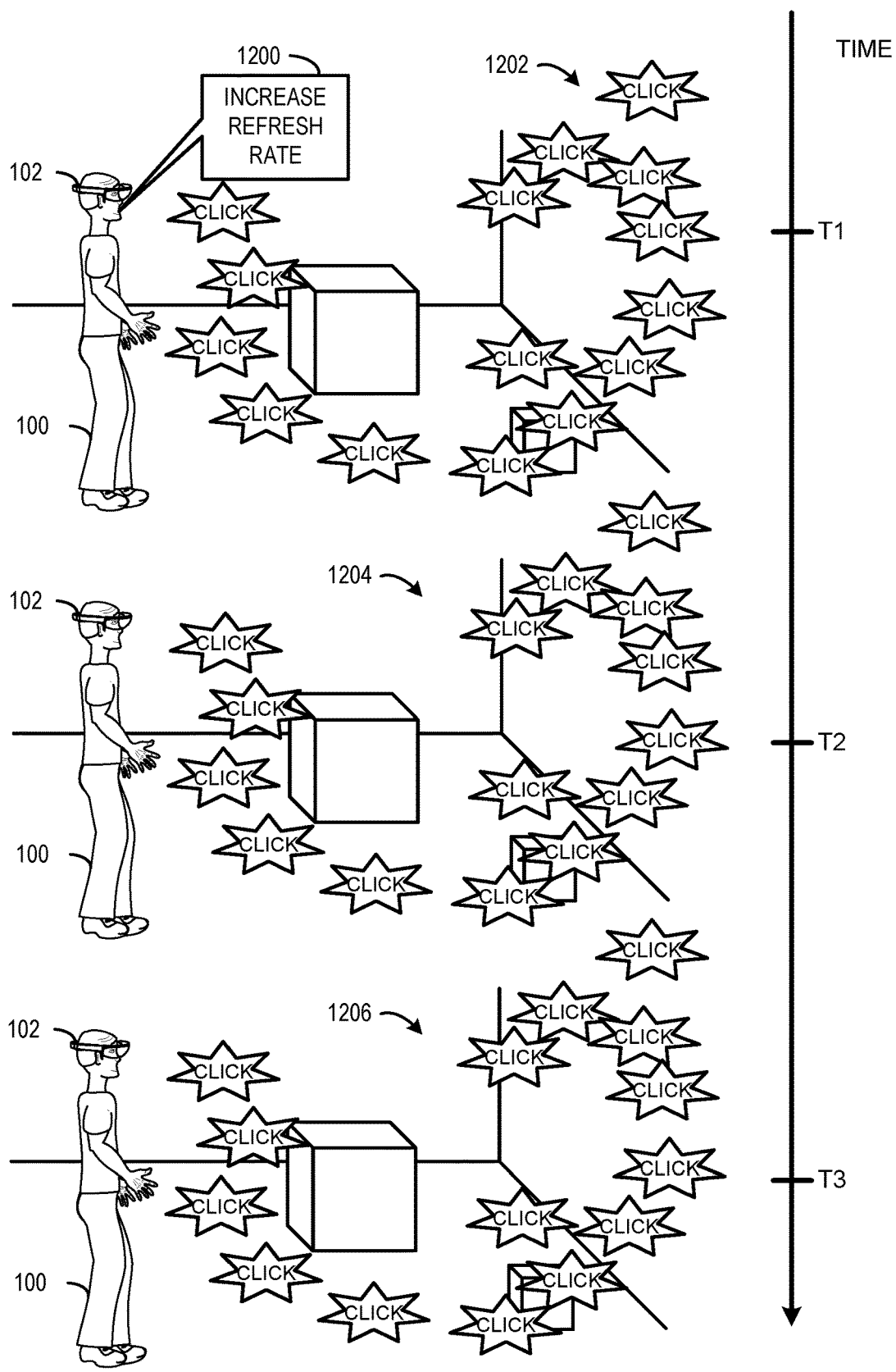

FIGS. 11-14 show example scenarios in which the head-mounted device dynamically adjusts the refresh rate at which the time-of-flight adjusted, spatialized audio signals are output to the speakers. FIGS. 11-12 show example scenarios in which the head-mounted device 102 is configured to dynamically adjust the refresh rate at which the time-of-flight adjusted, spatialized audio signals are output to the speakers based upon user input received from the wearer 100. In FIG. 11, the head-mounted device 102 detects a voice command 1100 from the wearer 100 in the form of the phrase "decrease refresh rate." The head-mounted device 102 is configured to set/dynamically adjust the refresh rate based upon receiving the voice command 1100 from the wearer 100. In this example, the head-mounted device 102 decreases the refresh rate based upon the voice command. At time T1, the head-mounted device 102 outputs a first set of time-of-flight adjusted, spatialized audio signals 1102. For simplicity, the first set of audio signals 1102 is depicted as occurring at the same time. In actuality, the first set audio signals 1102 is output over a window of time that is based on the time-of-flight adjustments. At time T3, the head-mounted device 102 outputs a second set of time-of-flight adjusted, spatialized audio signals 1104 per the decreased refresh rate.

In FIG. 12, the head-mounted device 102 detects a voice command 800 from the wearer 100 in the form of the phrase "increase refresh rate." The head-mounted device 102 is configured to set/dynamically adjust the refresh rate based upon receiving the voice command 1200 from the wearer 100. In this example, the head-mounted device 102 increases the refresh rate based upon the voice command. At time T1, the head-mounted device 102 outputs a first set of time-of-flight adjusted, spatialized audio signals 1202. At time T2, the head-mounted device 102 outputs a second set of time-of-flight adjusted, spatialized audio signals 1204. At time T3, the head-mounted device 102 outputs a third set of time-of-flight adjusted, spatialized audio signals 1206 per the increased refresh rate. In this example, the decreased refresh rate results in two sets of audio signals being output over the time frame T1-T3, and the increased refresh rate results in three sets of audio signals being output over the time frame T1-T3.

Figure 13:
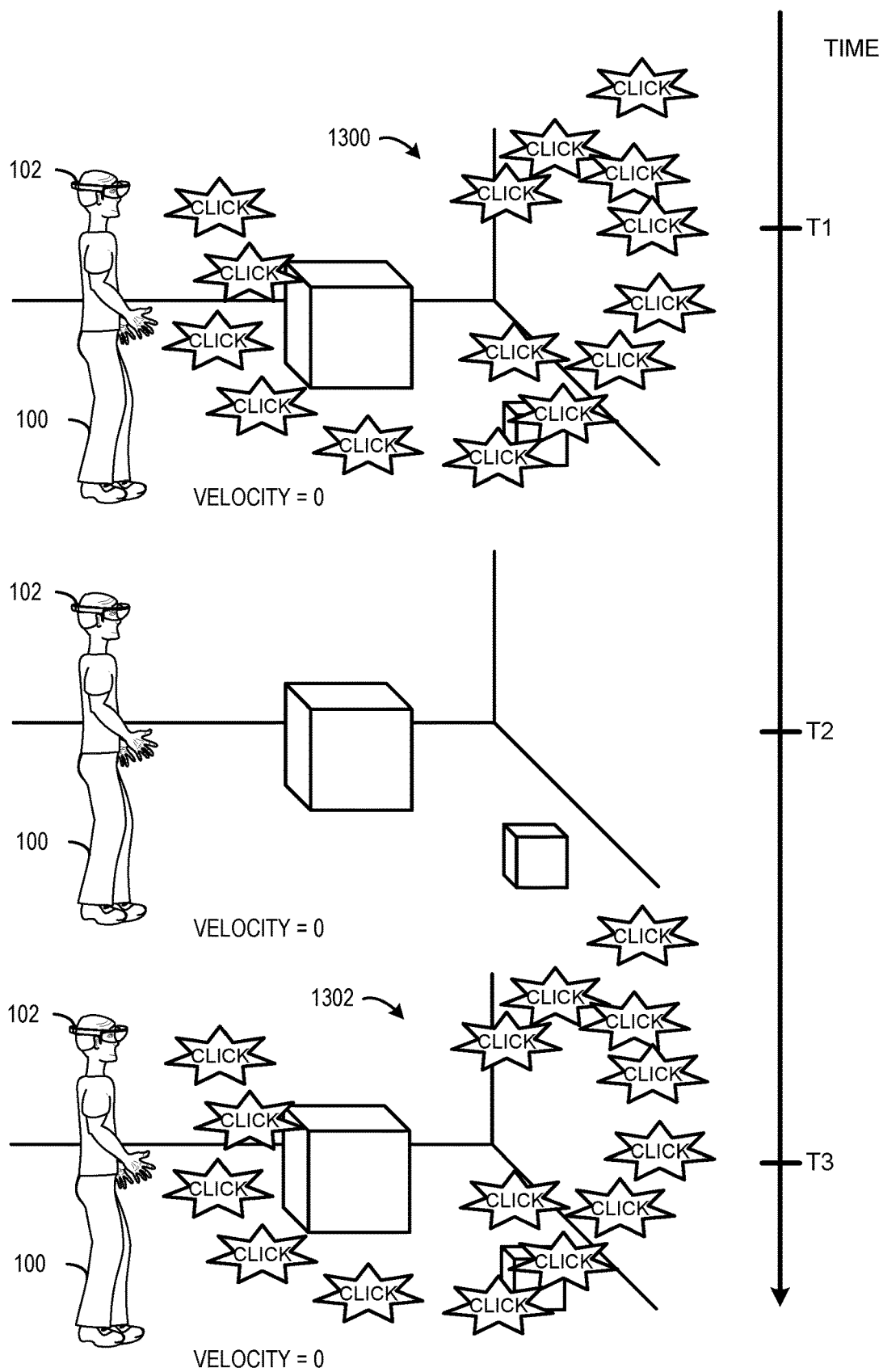
FIGS. 13 and 14 shows an example head-mounted device repeatedly outputting time-of-flight adjusted, spatialized audio signals according to a refresh rate that dynamically changes based upon one or more motion parameters of one or more motion sensors of the head-mounted device.
Figure 14:
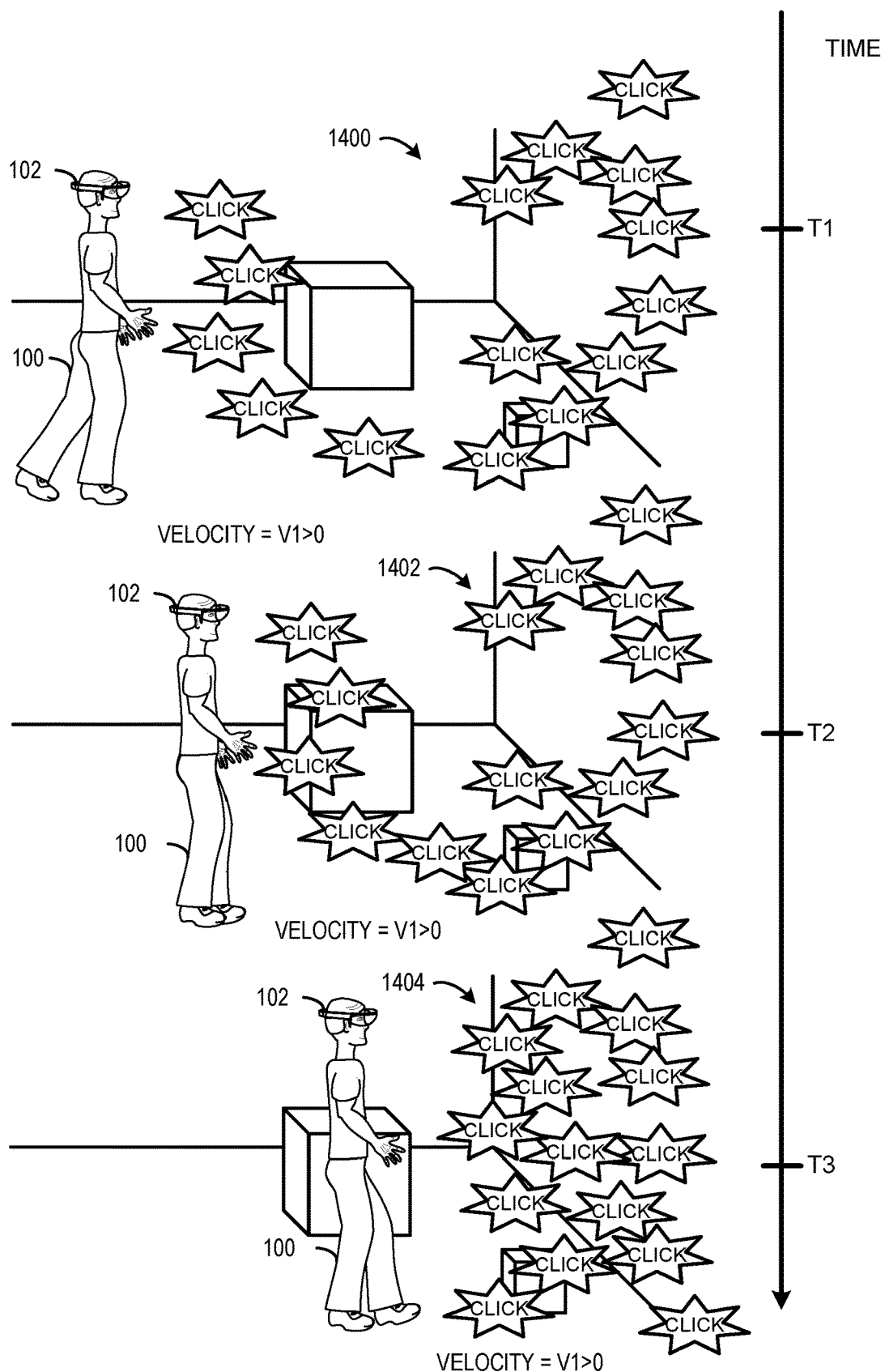

FIGS. 13-14 show example scenarios in which the head-mounted device 102 is configured to dynamically adjust the refresh rate at which the time-of-flight adjusted, spatialized audio signals are output to the speakers based upon one or more motion parameters from one or more motion sensors of the head-mounted device 102. In FIG. 13, a motion sensor of the head-mounted device 102 indicates that the velocity of the head-mounted device 102 is zero. In other words, the wearer 100 is standing still. The head-mounted device 102 is configured to set/dynamically adjust the refresh rate based upon the velocity. In this example, because the velocity is zero, the head-mounted device 102 decreases the refresh rate. At time T1, the head-mounted device 102 outputs a first set of time-of-flight adjusted, spatialized audio signals 130. At time T2, the velocity is still zero, so the refresh rate stays the same. At time T3, the velocity is still zero, and the head-mounted device 102 outputs a second set of time-of-flight adjusted, spatialized audio signals 1302 per the decreased refresh rate.

In FIG. 14, at time T1, the motion sensor of the head-mounted device 102 indicates that the velocity of the head-mounted device 102 is V1 which is greater than zero. In other words, the wearer 100 is moving throughout the physical environment 104. The head-mounted device 102 is configured to dynamically adjust the refresh rate based on the velocity. In this example, because the velocity is greater than zero, the head-mounted device 102 increases the refresh rate. More specifically, at time T1, the head-mounted device 102 outputs a first set of time-of-flight adjusted, spatialized audio signals 1400. At time T2, the velocity is still V1, so the increased refresh rate is maintained, and the head-mounted device 102 outputs a second set of time-of-flight adjusted, spatialized audio signals 1402. At time T3, the velocity is still V1, so the increased refresh rate is maintained, and the head-mounted device 102 outputs a third set of time-of-flight adjusted, spatialized audio signals 1404 per the increased refresh rate. In this example, the decreased refresh rate results in two sets of audio signals being output over the time frame T1-T3, and the increased refresh rate results in three sets of audio signals being output over the time frame T1-T3.

The refresh rate may be adjusted to any suitable period. For example, if the motion sensor indicates that the wearer is walking quickly, the refresh may be set to 250 milliseconds and if the motion sensor indicates that the wearer is stationary, then the refresh rate may be set to 2 seconds. In some implementations, the head-mounted device may be configured to select the refresh rate from a plurality of predefined refresh rates. Non-limiting examples of predefined refresh rates may include 0.25 seconds, 0.5 seconds, 1 second, and 2 seconds.

Figure 15:
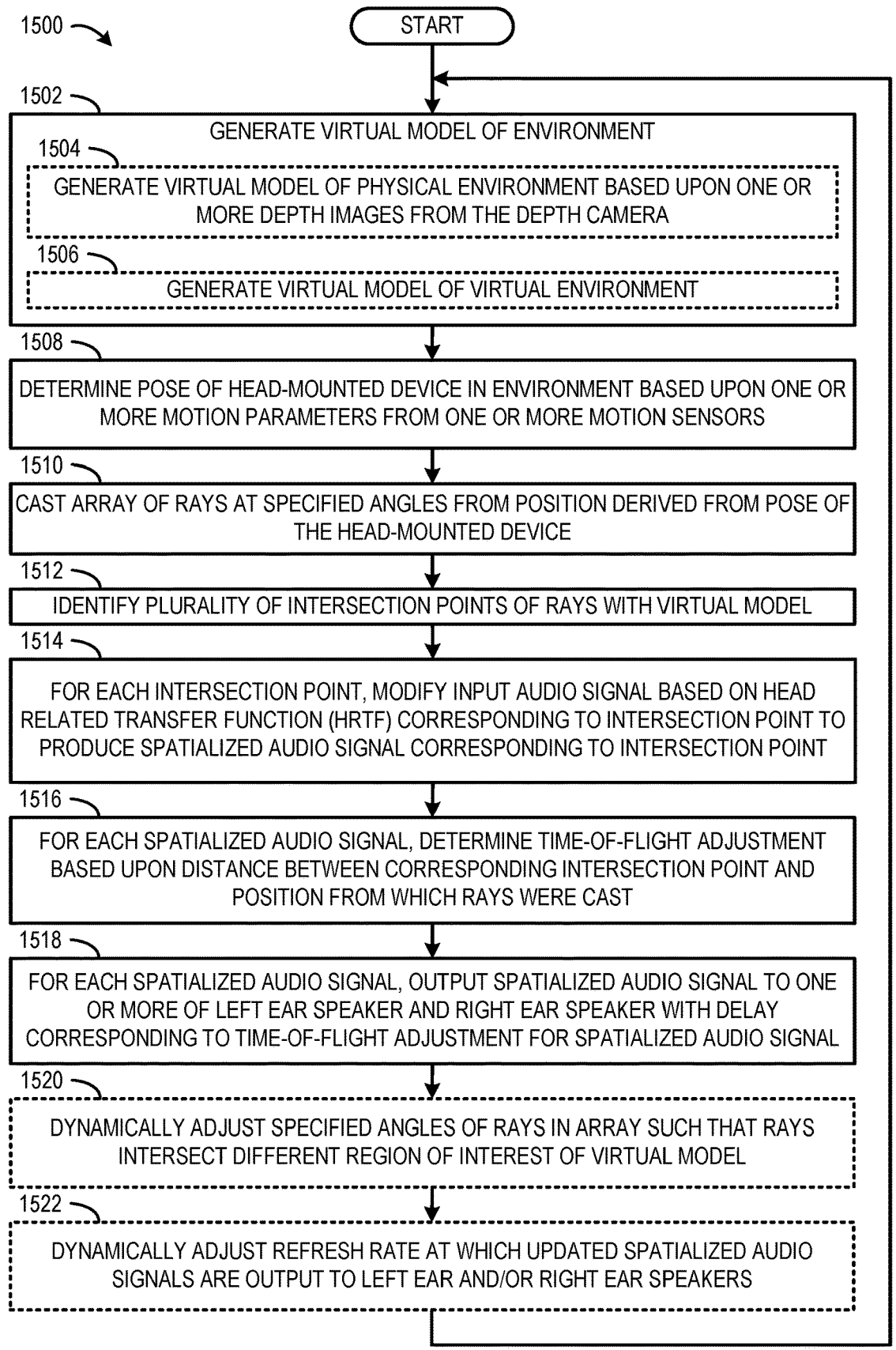
FIG. 15 shows an example method for performing virtual echolocation using a head-mounted device.

FIG. 15 shows an example method 1500 for performing virtual echolocation using a head-mounted device. For example, the method 1500 may be performed by the head-mounted device 102 of FIG. 1, the head-mounted device 1600 of FIG. 16, or the computing system 1700 of FIG. 17. At 1502, the method 1500 includes generating a virtual model of an environment. In some implementations, the virtual model may characterize a physical environment, and at 1504, the virtual model may be generated based upon one or more depth images from a depth camera. In some implementations, at 1506, the virtual model may characterize a virtual environment and may be generated in another manner. At 1508, the method 1500 includes determining a pose of the head-mounted device in the environment based upon one or more motion parameters from one or more motion sensors. At 1510, the method 1500 includes casting an array of rays at specified angles from a position derived from the pose. At 1512, the method 1500 includes identifying a plurality of intersection points of the rays with the virtual model. At 1514, the method 1500 includes, for each intersection point of the plurality of intersection points, modifying an input audio signal based on an HRTF corresponding to the intersection point to produce a spatialized audio signal corresponding to the intersection point. At 1516, the method 1500 includes, for each spatialized audio signal of a plurality of spatialized audio signals corresponding to the plurality of intersection points, determining a time-of-flight adjustment based upon a distance between the corresponding intersection point and the position from which the rays were cast. At 1518, the method 1500 includes, for each spatialized audio signal of the plurality of spatialized audio signals, outputting the spatialized audio signal to one or more of the left ear speaker and the right ear speaker with a delay corresponding to the time-of-flight adjustment for the spatialized audio signal.

In some implementations, at 1520, the method 1500 optionally may include dynamically adjusting the specified angles of the rays in the array such that the rays intersect a different region of interest of the virtual model. Additionally, in some implementations, at 1522, the method 1500 optionally may include dynamically adjusting a refresh rate at which a plurality of updated spatialized audio signal are output to the left ear and/or right ear speakers. The method 1500 returns to 1502 to repeatedly output a plurality of updated spatialized audio signals to the left ear and/or right ear speakers according to the refresh rate.

Figure 16:
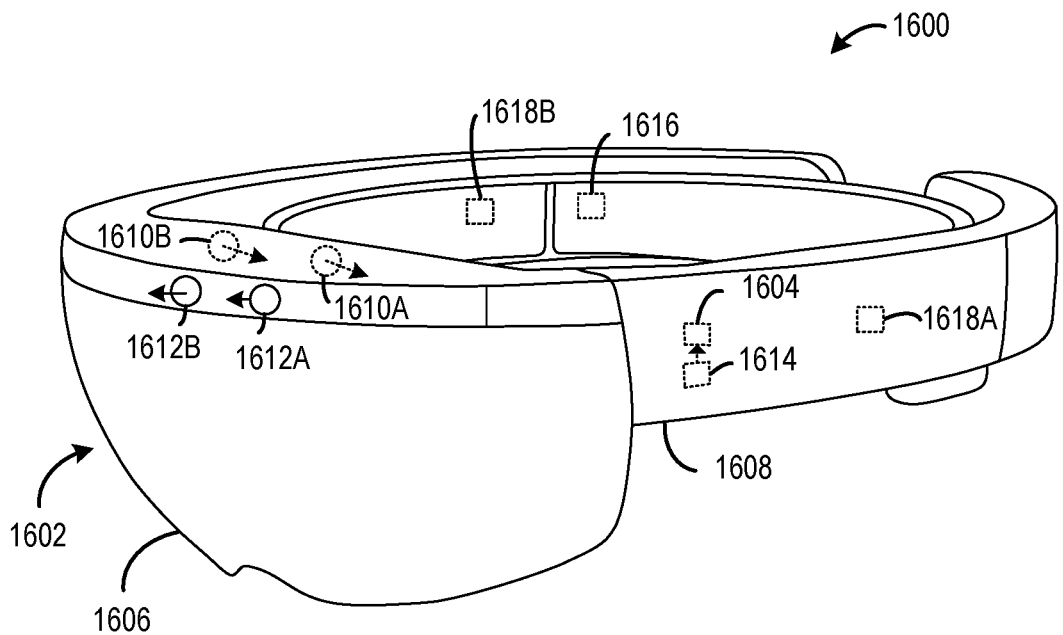
FIG. 16 shows an example head-mounted device.

FIG. 16 shows aspects of an example head-mounted device 1600. The head-mounted device 1600 is a non-limiting example of the head-mounted device 102 shown in FIG. 1, the computing system 1700 shown in FIG. 17, and/or other head-mounted devices disclosed herein. The head-mounted device 1600 may be configured to provide virtual echolocation to a wearer of the head-mounted device 1600.

In some implementations, the head-mounted device 1600 may include a near-eye display 1602 operably by an on-board computer 1604. The near-eye display 1602 may be wholly or partially transparent from the perspective of the wearer. In other implementations, the near-eye display may be wholly opaque. Any suitable mechanism may be used to display images via the near-eye display 1602. For example, the near-eye display 1602 may include image-producing elements located within lenses 1606. As another example, the near-eye display 1602 may include a display device, such as a liquid crystal on silicon (LCOS) device or OLED microdisplay located within a frame 1608. In this example, the lenses 1606 may serve as, or otherwise include, a light guide for delivering light from the display device to the eyes of a wearer. Additionally or alternatively, the near-eye display 1602 may present left-eye and right-eye virtual-reality images via respective left-eye and right-eye displays. In yet other implementations, the near-eye display 1602 may be omitted from the head-mounted device 1600.

The on-board computer 1604 may be configured to perform various operations related to receiving user input (e.g., gesture recognition, head position, gaze detection), providing time-of-flight adjusted, spatialized audio output, and other operations described herein. In some implementations, some to all of the computing functions described above, may be performed off board.

The head-mounted device 1600 includes various sensors and related systems to provide information to the on-board computer 1604. Such sensors may include, but are not limited to, inward facing image sensors 1610A and 1610B, outward facing image sensors 1612A and 1612B, an inertial measurement unit (IMU) 1614, and one or more microphones 1616. The one or more inward facing image sensors 1610A, 1610B may be configured to acquire gaze tracking information from a wearer's eyes. In some implementations, the inward facing image sensors 1610A, 1610B may be omitted from the head-mounted device 1600.

The one or more outward facing image sensors 1612A, 1612B may be configured to measure physical environment attributes of a physical environment. In one example, image sensor 1612A may include a light intensity camera configured to collect light intensity images of a physical environment. The image sensor 1612B may include a depth camera configured to collect depth images of a physical environment. More particularly, in one example, the depth camera is an infrared time-of-flight depth camera.

Data from the outward facing image sensors 1612A, 1612B may be used by the on-board computer 1604 to detect movements, such as gesture-based inputs or other movements performed by a wearer or by a person or physical object in the physical environment. In one example, data from the outward facing image sensors 1612A, 1612B may be used to detect a wearer input performed by the wearer of the virtual-reality computing system 1600, such as a gesture.

Furthermore, data from the outward facing image sensors 1612A, 1612B may be used by the on-board computer 1604 to determine direction/location and orientation data (e.g., from imaging environmental features) that enables position/motion tracking of the head-mounted device 1600 in the physical environment.

The IMU 1614 may be configured to provide position and/or orientation data of the head-mounted device 1600 to the on-board computer 1604. In one example, the IMU 1614 is a three-axis or three-degree of freedom (3DOF) position sensor system. Such a configuration may include three gyroscopes to indicate or measure a change in orientation of the head-mounted device 1600 within 3D space about three orthogonal axes (e.g., roll, pitch, and yaw).

In another example, the IMU 1614 is a six-axis or six-degree of freedom (6DOF) position sensor system. Such a configuration may include three accelerometers and three gyroscopes to indicate or measure a change in location of the head-mounted device 1600 along three orthogonal spatial axes (e.g., x, y, and z) and a change in device orientation about three orthogonal rotation axes (e.g., yaw, pitch, and roll). In some implementations, position and orientation data from the outward facing image sensors 1612A, 1612B and the IMU 1614 may be used in conjunction to determine a position and orientation (or 6DOF pose) of the head-mounted device 1600.

The head-mounted device 1600 may also support other suitable positioning techniques, such as GPS or other global navigation systems. Further, while specific examples of position sensor systems have been described, it will be appreciated that any other suitable sensor systems may be used. For example, head pose and/or movement data may be determined based on sensor information from any combination of sensors mounted on the wearer and/or external to the wearer including, but not limited to, any number of gyroscopes, accelerometers, inertial measurement units, GPS devices, barometers, magnetometers, cameras (e.g., visible light cameras, infrared light cameras, time-of-flight depth cameras, structured light depth cameras, etc.), communication devices (e.g., WIFI antennas/interfaces), etc.

The one or more microphones 1616 may be configured to measure sound in the physical environment. For example, audio data from the one or more microphones 1616 may be used by the on-board computer 1604 to recognize voice commands provided by the wearer to control the head-mounted device 1600.

The head-mounted device 1600 includes a left ear speaker 1618A and a right ear speaker 1618B. The speakers 1618A and 1618B are coupled to the frame 1608 such that the speakers 1618A and 1618B are positioned above and behind left and right ears of a wearer of the head-mounted device 1600. The on-board computer 1604 may be configured to output spatialized audio signals to one or more of the left ear speaker 1618A and the right ear speaker 1618B with a delay corresponding to a time-of-flight adjustment for the spatialized audio signal. The time-of-flight adjusted, spatialized audio signals may be repeatedly output by the speakers 1618A and 1618B to provide virtual echolocation to the wearer of the head-mounted device 1600.

The on-board computer 1604 may include a logic machine and a storage machine in communication with the various sensors of the head-mounted device 1600 as well as the speakers, and discussed in more detail below with respect to FIG. 17.

The examples disclosed herein may be applicable to other hardware configurations as well. For example, the virtual echolocation approaches discussed herein may be used with a video game (or other application), such as in the form of a software plug-in. The video game may have an accessibility mode that may be accessed to activate the echolocation audio signals. In this mode, the software plug-in may query a virtual game map that defines a 3D virtual environment of the video game instead of the depth sensors to identify audio beacon intersection points in the virtual game map. The resulting spatialized audio signals would be communicated to the user in the same way to convey the distance to the virtual objects in the virtual game map of the video game. In this implementation, the spatialized audio signal may be output to left ear and right ear speakers of headphones worn by the user. Such a configuration may allow a visually-impaired user to navigate the 3D virtual environment of the video game world by listening to the echolocation audio signals. This approach may enable the user to participate in social gaming experiences from which the user would have been previously excluded due to the user being unable to see the 3D virtual environment being visually presented. Further, such a configuration may serve as a training ground for the user to learn echolocation skills that could also be applied to the real world.

Figure 17:
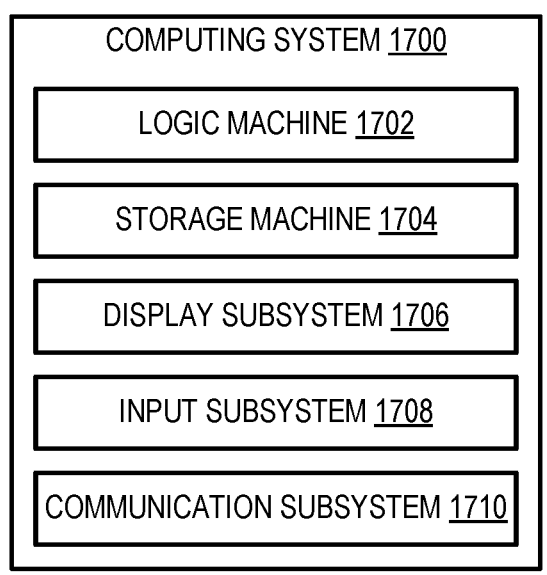
FIG. 17 shows an example computing system.

FIG. 17 schematically shows a non-limiting implementation of a computing system 1700 that can enact one or more of the methods and processes described above. Computing system 1700 is shown in simplified form. Computing system 1700 may take the form of one or more personal computers, server computers, tablet computers, home-entertainment computers, network computing devices, gaming devices, mobile computing devices, mobile communication devices (e.g., smart phone), virtual-reality devices, head-mounted devices, and/or other computing devices. For example, the computing system 1700 may be a non-limiting example of the head-mounted device 102 of FIG. 1 and/or the head-mounted device 1600 of FIG. 16.

Computing system 1700 includes a logic machine 1702 and a storage machine 1704. Computing system 1700 may optionally include a display subsystem 1706, input subsystem 1708, communication subsystem 1710, and/or other components not shown in FIG. 17.

Logic machine 1702 includes one or more physical devices configured to execute instructions. For example, the logic machine 1702 may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

The logic machine 1702 may include one or more processors configured to execute software instructions. Additionally or alternatively, the logic machine 1702 may include one or more hardware or firmware logic machines configured to execute hardware or firmware instructions. Processors of the logic machine 1702 may be single-core or multi-core, and the instructions executed thereon may be configured for sequential, parallel, and/or distributed processing. Individual components of the logic machine 1702 optionally may be distributed among two or more separate devices, which may be remotely located and/or configured for coordinated processing. Aspects of the logic machine 1702 may be virtualized and executed by remotely accessible, networked computing devices configured in a cloud-computing configuration.

Storage machine 1704 includes one or more physical devices configured to hold instructions executable by the logic machine 1702 to implement the methods and processes described herein. When such methods and processes are implemented, the state of storage machine 1704 may be transformed—e.g., to hold different data.

Storage machine 1704 may include removable and/or built-in devices. Storage machine 1704 may include optical memory (e.g., CD, DVD, HD-DVD, Blu-Ray Disc, etc.), semiconductor memory (e.g., RAM, EPROM, EEPROM, etc.), and/or magnetic memory (e.g., hard-disk drive, floppy-disk drive, tape drive, MRAM, etc.), among others. Storage machine 1704 may include volatile, nonvolatile, dynamic, static, read/write, read-only, random-access, sequential-access, location-addressable, file-addressable, and/or content-addressable devices.

It will be appreciated that storage machine 1704 includes one or more physical devices. However, aspects of the instructions described herein alternatively may be propagated by a communication medium (e.g., an electromagnetic signal, an optical signal, etc.) that is not held by a physical device for a finite duration.

Aspects of logic machine 1702 and storage machine 1704 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

When included, display subsystem 1706 may be used to present a visual representation of data held by storage machine 1704. This visual representation may take the form of a graphical user interface (GUI). As the herein described methods and processes change the data held by the storage machine, and thus transform the state of the storage machine, the state of display subsystem 1706 may likewise be transformed to visually represent changes in the underlying data. Display subsystem 1706 may include one or more display devices utilizing virtually any type of technology. Such display devices may be combined with logic machine 1702 and/or storage machine 1704 in a shared enclosure, or such display devices may be peripheral display devices. As a non-limiting example, display subsystem 1706 may include the near-eye displays described above.

When included, input subsystem 1708 may comprise or interface with one or more user-input devices such as a keyboard, mouse, touch screen, or game controller. In some implementations, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity.

When included, communication subsystem 1710 may be configured to communicatively couple computing system 1700 with one or more other computing devices. Communication subsystem 1710 may include wired and/or wireless communication devices compatible with one or more different communication protocols. As non-limiting examples, the communication subsystem may be configured for communication via a wireless telephone network, or a wired or wireless local- or wide-area network. In some implementations, the communication subsystem 1710 may allow computing system 1700 to send and/or receive messages to and/or from other devices via a network such as the Internet.

In some implementations, the computing system 1700 may provide virtual echolocation to navigate a virtual game map that defines a 3D virtual environment of a video game. In such implementations, the virtual game map may server as the virtual model in which intersection points are identified. Further, the resulting time-of-flight adjusted, spatialized audio signals may be output to left ear and right ear speakers of headphones worn by the user and connected to the computing system 1700. Such a configuration may allow a visually-impaired user to navigate the 3D virtual environment of the video game world by listening to the echolocation audio signals output to the headphones. Moreover, the headphones may communicate with the computing device 1700 in any suitable manner, and the computing device 1700 need not be mounted to the user's head. Instead, the computing device 1700 may be remotely located relative to the user.

In an example, a head-mounted device, comprises a depth camera configured to image a physical environment, one or more motion sensors configured to measure one or more motion parameters, a left ear speaker and a right ear speaker, a processing system, and a storage system holding instructions executable by the processing system to generate a virtual model of the physical environment based upon one or more depth images from the depth camera, determine a pose of the head-mounted device in the physical environment based upon the one or more motion parameters from the one or more motion sensors, cast an array of rays at specified angles from a position derived from the pose of the head-mounted device, identify a plurality of intersection points of the rays with the virtual model, for each intersection point of the plurality of intersection points, modify an input audio signal based on a head related transfer function (HRTF) corresponding to the intersection point to produce a spatialized audio signal corresponding to the intersection point, for each spatialized audio signal of a plurality of spatialized audio signals corresponding to the plurality of intersection points, determine a time-of-flight adjustment based upon a distance between the corresponding intersection point and the position from which the rays were cast, and for each spatialized audio signal of the plurality of spatialized audio signals, output the spatialized audio signal to one or more of the left ear speaker and the right ear speaker with a delay corresponding to the time-of-flight adjustment for the spatialized audio signal. In this example and/or other examples, the storage system may further hold instructions executable by the processing system to modify the input audio signal by one or more of changing a volume of the input audio signal to account for a position in the physical environment corresponding to the intersection point from which the spatialized audio signal emanates and changing a directionality of the audio signal to account for a position in the physical environment corresponding to the intersection point from which the spatialized audio signal emanates. In this example and/or other examples, the storage system may further hold instructions executable by the processing system to repeatedly output a plurality of updated spatialized audio signals to the left ear and/or right ear speakers according to a refresh rate, wherein the plurality of updated spatialized audio signals are based upon an updated pose of the head-mounted device. In this example and/or other examples, the storage system may further hold instructions executable by the processing system to dynamically adjust the refresh rate based upon receiving user input from a wearer of the head-mounted device. In this example and/or other examples, the storage system may further hold instructions executable by the processing system to dynamically adjust the refresh rate based upon the one or more motion parameters from the one or more motion sensors. In this example and/or other examples, the storage system may further hold instructions executable by the processing system to dynamically adjust the specified angles of the rays in the array such that the rays intersect a different region of interest of the virtual model. In this example and/or other examples, the storage system may further hold instructions executable by the processing system to dynamically adjust the specified angles of the rays in the array based upon one or more of a position of a detected object in the physical environment nearest to the pose of the head-mounted device, a pose vector of the head-mounted device, and the one or more motion parameters from the motion sensors. In this example and/or other examples, the storage system may further hold instructions executable by the processing system to dynamically adjust the specified angles of the rays in the array based upon user input received from a wearer of the head-mounted device. In this example and/or other examples, the audio signal may be a first audio signal, and the storage system may further hold instructions executable by the processing system to cast one or more additional rays each having a specified angle and a specified length from the position, identify one or more additional intersection points of the one or more additional rays with the virtual model, for each of the one or more additional intersection points, modify a second, different audio signal based on a head related transfer function (HRTF) corresponding to the additional intersection point to produce a second spatialized audio signal corresponding to the intersection point, for each of one or more second spatialized audio signals corresponding to the one or more additional identified intersection points, determine a time-of-flight adjustment based upon a distance between the corresponding additional intersection point and the position, and for each of the one or more second spatialized audio signals, output the second spatialized audio signal to one or more of the left ear speaker and the right ear speaker with a delay corresponding to the time-of-flight adjustment for the spatialized audio signal.

In an example, a method for performing virtual echolocation using a computing device in communication with a left ear speaker, and a right ear speaker comprises generating a virtual model of an environment, determining a pose in the environment, casting an array of rays at specified angles from a position derived from the pose, identifying a plurality of intersection points of the rays with the virtual model, for each intersection point of the plurality of intersection points, modifying an input audio signal based on a head related transfer function (HRTF) corresponding to the intersection point to produce a spatialized audio signal corresponding to the intersection point, for each spatialized audio signal of a plurality of spatialized audio signals corresponding to the plurality of intersection points, determining a time-of-flight adjustment based upon a distance between the corresponding intersection point and the position from which the rays were cast, and for each spatialized audio signal of the plurality of spatialized audio signals, outputting the spatialized audio signal to one or more of the left ear speaker and the right ear speaker with a delay corresponding to the time-of-flight adjustment for the spatialized audio signal. In this example and/or other examples, the environment may be a physical environment, the computing device may further include a depth camera configured to image the physical environment and one or more motion sensors configured to measure one or more motion parameters, the virtual model of the physical environment may be generated based upon one or more depth images from the depth camera, and the pose may be determined based upon the one or more motion parameters of the one or more motion sensors. In this example and/or other examples, the environment may be a virtual environment, and the pose may be a virtual position in the virtual model of the virtual environment. In this example and/or other examples, the method may further comprise repeatedly outputting a plurality of updated spatialized audio signals to the left ear and/or right ear speakers according to a refresh rate, wherein the plurality of updated spatialized audio signals are based upon an updated pose in the environment. In this example and/or other examples, the method may further comprise dynamically adjusting the refresh rate based upon one or more of user input received from a user of the computing device and the one or more motion parameters from the one or more motion sensors. In this example and/or other examples, the method may further comprise, dynamically adjusting the specified angles of the rays in the array such that the rays intersect a different region of interest of the virtual model. In this example and/or other examples, the specified angles of the rays in the array may be dynamically adjusted based upon one or more of a position of a detected object in the physical environment nearest to the pose, a pose vector, one or more motion parameters from one or more motion sensors of the computing device, and user input received from a user of the computing device.

In an example, a head-mounted device comprises a depth camera configured to image a physical environment, one or more motion sensors configured to measure one or more motion parameters, a left ear speaker and a right ear speaker, a processing system, and a storage system holding instructions executable by the processing system to generate a virtual model of the physical environment based upon one or more depth images from the depth camera, determine a pose of the head-mounted device in the physical environment based upon the one or more motion parameters from the one or more motion sensors, cast an array of rays at specified angles from a position derived from the pose of the head-mounted device, wherein the specified angles are dynamically adjustable based upon one or more of user input received from the wearer and the one or more motion parameters from the one or more motion sensors, identify a plurality of intersection points of the rays with the virtual model, for each intersection point of the plurality of intersection points, modify an input audio signal based on a head related transfer function (HRTF) corresponding to the intersection point to produce a spatialized audio signal corresponding to the intersection point, for each spatialized audio signal of a plurality of spatialized audio signals corresponding to the plurality of intersection points, determine a time-of-flight adjustment based upon a distance between the corresponding intersection point and the position from which the rays were cast, and for each spatialized audio signal of the plurality of spatialized audio signals, output the spatialized audio signal to one or more of the left ear speaker and the right ear speaker with a delay corresponding to the time-of-flight adjustment for the spatialized audio signal. In this example and/or other examples, the storage system may further hold instructions executable by the processing system to repeatedly output a plurality of updated spatialized audio signals to the left ear and/or right ear speakers according to a refresh rate, wherein the plurality of updated spatialized audio signals are based upon an updated pose of the head-mounted device. In this example and/or other examples, the storage system may further hold instructions executable by the processing system to dynamically adjust the refresh rate based upon one or more of receiving user input from a wearer of the head-mounted device and the one or more motion parameters from the one or more motion sensors. In this example and/or other examples, the audio signal may be a first audio signal, and the storage system may further hold instructions executable by the processing system to cast one or more additional rays each having a specified angle and a specified length from the position, identify one or more additional intersection points of the one or more additional rays with the virtual model, for each of the one or more additional intersection points, modify a second, different audio signal based on a head related transfer function (HRTF) corresponding to the additional intersection point to produce a second spatialized audio signal corresponding to the intersection point, for each of one or more second spatialized audio signals corresponding to the one or more additional identified intersection points, determine a time-of-flight adjustment based upon a distance between the corresponding additional intersection point and the position, and for each of the one or more second spatialized audio signals, output the second spatialized audio signal to one or more of the left ear speaker and the right ear speaker with a delay corresponding to the time-of-flight adjustment for the spatialized audio signal.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. A head-mounted device, comprising:
 a depth camera configured to image a physical environment;
 one or more motion sensors configured to measure one or more motion parameters;
 a left ear speaker and a right ear speaker;
 a processing system; and
 a storage system holding instructions executable by the processing system to
  generate a virtual model of the physical environment based upon one or more depth images from the depth camera;
  determine a pose of the head-mounted device in the physical environment based upon the one or more motion parameters from the one or more motion sensors;
  cast an array of rays at specified angles from a position derived from the pose of the head-mounted device, wherein each ray has a fixed length;
  identify a plurality of intersection points of the rays with the virtual model;
  for each intersection point of the plurality of intersection points, modify an input audio signal based on a head related transfer function corresponding to the intersection point to produce a spatialized audio signal corresponding to the intersection point;
  for each spatialized audio signal of a plurality of spatialized audio signals corresponding to the plurality of intersection points, determine a time-of-flight adjustment based upon a distance between the corresponding intersection point and the position from which the rays were cast; and
  for each spatialized audio signal of the plurality of spatialized audio signals, output the spatialized audio signal to one or more of the left ear speaker and the right ear speaker with a delay corresponding to the time-of-flight adjustment for the spatialized audio signal.

2. The head-mounted device of claim 1, wherein each of the rays of the array have a same length.

3. The head-mounted-device of claim 1, wherein the position approximates a position of a user's mouth when the user is wearing the head-mounted device and, wherein each of the rays of the array is cast downward from the position.

4. The head-mounted device of claim 1, wherein the array of rays form a semicircular perimeter in front of a user when the user is wearing the head-mounted device.

5. The head-mounted device of claim 1, wherein the storage system further holds instructions executable by the processing system not to output a spatialized audio signal corresponding to a ray of the array based on the ray not intersecting an object.

6. The head-mounted device of claim 1, wherein the storage system further holds instructions executable by the processing system to modify the input audio signal by one or more of changing a volume of the input audio signal to account for a position in the physical environment corresponding to the intersection point from which the spatialized audio signal emanates and changing a directionality of the audio signal to account for a position in the physical environment corresponding to the intersection point from which the spatialized audio signal emanates.

7. The head-mounted device of claim 1, wherein the storage system further holds instructions executable by the processing system to repeatedly output a plurality of updated spatialized audio signals to the left ear and/or right ear speakers according to a refresh rate, wherein the plurality of updated spatialized audio signals are based upon an updated pose of the head-mounted device.

8. The head-mounted device of claim 7, wherein the storage system further holds instructions executable by the processing system to dynamically adjust the refresh rate based upon receiving user input from a wearer of the head-mounted device.

9. The head-mounted device of claim 7, wherein the storage system further holds instructions executable by the processing system to dynamically adjust the refresh rate based upon the one or more motion parameters from the one or more motion sensors.

10. The head-mounted device of claim 1, wherein the audio signal is a first audio signal, and wherein the storage system further holds instructions executable by the processing system to cast an additional array of rays at specified angles from the position;
 identify a plurality of additional intersection points of a plurality of rays of the additional array with the virtual model;
 for each of the plurality of additional intersection points, modify a second, different audio signal based on a head related transfer function corresponding to the additional intersection point to produce a second spatialized audio signal corresponding to the intersection point;
 for each of one or more second spatialized audio signals corresponding to the one or more additional identified intersection points, determine a time-of-flight adjustment based upon a distance between the corresponding additional intersection point and the position; and
 for each of the one or more second spatialized audio signals, output the second spatialized audio signal to one or more of the left ear speaker and the right ear speaker with a delay corresponding to the time-of-flight adjustment for the spatialized audio signal.

11. A method for performing virtual echolocation using a computing device in communication with a left ear speaker, and a right ear speaker, the method comprising:
  generating a virtual model of a physical environment;
  determining a pose in the environment;
  casting an array of rays at specified angles from a position derived from the pose, wherein each ray has a fixed length;
  identifying a plurality of intersection points of the rays with the virtual model;
  for each intersection point of the plurality of intersection points, modifying an input audio signal based on a head related transfer function corresponding to the intersection point to produce a spatialized audio signal corresponding to the intersection point;
  for each spatialized audio signal of a plurality of spatialized audio signals corresponding to the plurality of intersection points, determining a time-of-flight adjustment based upon a distance between the corresponding intersection point and the position from which the rays were cast; and
  for each spatialized audio signal of the plurality of spatialized audio signals, outputting the spatialized audio signal to one or more of the left ear speaker and the right ear speaker with a delay corresponding to the time-of-flight adjustment for the spatialized audio signal.

12. The method of claim 11, wherein the computing device further includes a depth camera configured to image the physical environment and one or more motion sensors configured to measure one or more motion parameters, wherein the virtual model of the physical environment is generated based upon one or more depth images from the depth camera, and wherein the pose is determined based upon the one or more motion parameters of the one or more motion sensors.

13. The method of claim 11, further comprising:
  repeatedly outputting a plurality of updated spatialized audio signals to the left ear and/or right ear speakers according to a refresh rate, wherein the plurality of updated spatialized audio signals are based upon an updated pose in the environment.

14. The method of claim 13, further comprising:
  dynamically adjusting the refresh rate based upon one or more of user input received from a user of the computing device and the one or more motion parameters from the one or more motion sensors.

15. The method of claim 11, wherein each of the rays of the array have a same length.

16. The method of claim 11, wherein the position approximates a position of a user's mouth when the user is wearing the head-mounted device, and wherein each of the rays of the array is cast downward from the position.

17. The method of claim 11, wherein the array of rays form a semicircular perimeter in front of a user when the user is wearing the head-mounted device.

18. The method of claim 11, further comprising:
  not outputting a spatialized audio signal corresponding to a ray of the array based on the ray not intersecting an object.

19. A head-mounted device, comprising:
  a depth camera configured to image a physical environment;
  one or more motion sensors configured to measure one or more motion parameters;
  a left ear speaker and a right ear speaker;
  a processing system; and
  a storage system holding instructions executable by the processing system to:
    generate a virtual model of the physical environment based upon one or more depth images from the depth camera;
    determine a pose of the head-mounted device in the physical environment based upon the one or more motion parameters from the one or more motion sensors;
    cast an array of rays at specified angles from a position derived from the pose of the head-mounted device, wherein each ray has a fixed length;
    identify a plurality of intersection points of the rays with the virtual model;
    for each intersection point of the plurality of intersection points, modify an input audio signal based on a head related transfer function corresponding to the intersection point to produce a spatialized audio signal corresponding to the intersection point;
    for each spatialized audio signal of a plurality of spatialized audio signals corresponding to the plurality of intersection points, determine a time-of-flight adjustment based upon a distance between the corresponding intersection point and the position from which the rays were cast;
    for each spatialized audio signal of the plurality of spatialized audio signals, output the spatialized audio signal to one or more of the left ear speaker and the right ear speaker with a delay corresponding to the time-of-flight adjustment for the spatialized audio signal; and
    repeatedly output a plurality of updated spatialized audio signals to the left ear and/or right ear speakers according to a refresh rate, wherein the plurality of updated spatialized audio signals are based upon an updated pose of the head-mounted device.

20. The head-mounted device of claim 19, wherein the audio signal is a first audio signal, and wherein the storage system further holds instructions executable by the processing system to
  cast an additional array of rays at specified angles from the position;
  identify a plurality of additional intersection points of a plurality of rays of the additional array with the virtual model;
  for each of the plurality of additional intersection points, modify a second, different audio signal based on a head related transfer function corresponding to the additional intersection point to produce a second spatialized audio signal corresponding to the intersection point;
  for each of one or more second spatialized audio signals corresponding to the one or more additional identified intersection points, determine a time-of-flight adjustment based upon a distance between the corresponding additional intersection point and the position; and
  for each of the one or more second spatialized audio signals, output the second spatialized audio signal to one or more of the left ear speaker and the right ear speaker with a delay corresponding to the time-of-flight adjustment for the spatialized audio signal.

* * * * *